United States Patent
Blackburn et al.

(10) Patent No.: US 11,449,949 B2
(45) Date of Patent: *Sep. 20, 2022

(54) SYSTEM FOR MANAGEMENT OF INSURANCE RISK AND INSURANCE EVENTS

(71) Applicant: Scientia Potentia Est, LLC., Charleston, SC (US)

(72) Inventors: Jeremy Blackburn, Charleston, SC (US); Tim McVicker, Charleston, SC (US); Justin Southward, Charleston, SC (US); W. Kurt Taylor, N. Charleston, SC (US); Karl David, Charleston, SC (US); Austi Critchfield, Clearwater, FL (US); Michael Lu, N. Charleston, SC (US)

(73) Assignee: Scientia Potentia Est, LLC., Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/997,840

(22) Filed: Aug. 19, 2020

(65) Prior Publication Data

US 2021/0035231 A1    Feb. 4, 2021

Related U.S. Application Data

(63) Continuation-in-part of application No. 16/994,585, filed on Aug. 15, 2020, now Pat. No. 11,232,652, (Continued)

(51) Int. Cl.
G06Q 40/08    (2012.01)
G06Q 50/08    (2012.01)
(Continued)

(52) U.S. Cl.
CPC ........... G06Q 40/08 (2013.01); A61B 5/6887 (2013.01); B64C 39/024 (2013.01); B64D 47/08 (2013.01);
(Continued)

(58) Field of Classification Search
CPC .. G06Q 40/08; G06Q 10/0875; G06Q 10/103; G06Q 10/1057; G06Q 10/109;
(Continued)

(56) References Cited

U.S. PATENT DOCUMENTS

| 1,059,298 A | 4/1913 | Hoyne |
| 7,031,930 B2 | 4/2006 | Freeman et al. |

(Continued)

FOREIGN PATENT DOCUMENTS

| EP | 3617824 A1 | 4/2020 |
| WO | 2018163044 | 9/2018 |
| WO | 2018177568 | 10/2018 |

OTHER PUBLICATIONS

Hughes, Dave, The Impact of Blockchain Technology on the Construction Industry:, Feb. 19, 2017; medium.com, 8 pages. (Year: 2017).

(Continued)

*Primary Examiner* — Garcia Ade
(74) *Attorney, Agent, or Firm* — Kim and Lahey Law Firm, LLC; Douglas W. Kim

(57) ABSTRACT

This system is directed to the management of insurance information, risks and coverage, wherein a set of non-transitory computer readable instructions included in a kiosk disposed at the construction site can include instructions for creating a certificate of insurance according to a determination that the insurance requirements have been met and storing the certificate of insurance in the distributed ledger.

31 Claims, 32 Drawing Sheets

Related U.S. Application Data which is a continuation-in-part of application No. 16/991,916, filed on Aug. 12, 2020, now Pat. No. 11,216,823, which is a continuation-in-part of application No. 16/876,080, filed on May 17, 2020, which is a continuation-in-part of application No. 16/810,782, filed on Mar. 5, 2020, now Pat. No. 11,216,781, which is a continuation-in-part of application No. 16/510,634, filed on Jul. 12, 2019, now Pat. No. 10,713,737, which is a continuation-in-part of application No. 16/452,076, filed on Jun. 25, 2019, now abandoned, said application No. 16/810,782 is a continuation-in-part of application No. 16/510,642, filed on Jul. 12, 2019, now Pat. No. 11,216,772, which is a continuation-in-part of application No. 16/452,076, filed on Jun. 25, 2019, now abandoned, said application No. 16/810,782 is a continuation-in-part of application No. 16/452,076, filed on Jun. 25, 2019, now abandoned.

(51) Int. Cl.
| | |
|---|---|
| *G06Q 10/10* | (2012.01) |
| *G06Q 50/26* | (2012.01) |
| *G16H 40/67* | (2018.01) |
| *G16H 50/30* | (2018.01) |
| *G06Q 40/00* | (2012.01) |
| *G06Q 10/08* | (2012.01) |
| *G06K 19/07* | (2006.01) |
| *B64C 39/02* | (2006.01) |
| *B64D 47/08* | (2006.01) |
| *H04N 5/76* | (2006.01) |
| *A61B 5/00* | (2006.01) |
| *G06V 20/40* | (2022.01) |

(52) U.S. Cl.
CPC ..... *G06K 19/0723* (2013.01); *G06Q 10/0875* (2013.01); *G06Q 10/103* (2013.01); *G06Q 10/109* (2013.01); *G06Q 10/1057* (2013.01); *G06Q 40/125* (2013.12); *G06Q 50/08* (2013.01); *G06Q 50/265* (2013.01); *G06V 20/41* (2022.01); *G16H 40/67* (2018.01); *G16H 50/30* (2018.01); *H04N 5/76* (2013.01); *A61B 2503/20* (2013.01); *B64C 2201/127* (2013.01); *G06V 20/44* (2022.01)

(58) Field of Classification Search
CPC .... G06Q 40/125; G06Q 50/08; G06Q 50/265; A61B 5/6887; A61B 2503/20; B64C 39/024; B64C 2201/127; B64D 47/08; G06K 9/00718; G06K 19/0723; G06K 2009/00738; G06K 9/00288; G06K 9/00771; G16H 40/67; G16H 50/30; G16H 40/20; H04N 5/76; H04N 5/77; G06V 20/41; G06V 20/44; G06V 20/52; G06V 40/172
USPC ............................................................ 705/4
See application file for complete search history.

(56) References Cited

U.S. PATENT DOCUMENTS

| | | | |
|---|---|---|---|
| 7,330,821 | B2 | 2/2008 | Wares |
| 7,508,973 | B2 | 3/2009 | Okabe et al. |
| 7,546,576 | B2 | 6/2009 | Egli |
| 7,898,403 | B2 | 3/2011 | Ritter et al. |
| 8,004,397 | B2 | 8/2011 | Forrest et al. |
| 8,103,596 | B1 | 1/2012 | McFarlin et al. |
| 8,321,302 | B2 | 11/2012 | Bauer et al. |
| 8,428,904 | B2 | 4/2013 | Sock et al. |
| 8,521,620 | B2 | 8/2013 | Livingston et al. |
| 9,135,787 | B1 | 9/2015 | Russell et al. |
| 9,727,923 | B2 | 8/2017 | Teh et al. |
| 10,121,112 | B1 | 11/2018 | Vasquez, Jr. et al. |
| 10,338,913 | B2 * | 7/2019 | Franchitti .............. G06N 5/022 |
| 2006/0137015 | A1 | 6/2006 | Fahrny et al. |
| 2007/0220342 | A1 | 9/2007 | Vieira et al. |
| 2010/0058364 | A1 | 3/2010 | Sherrill et al. |
| 2011/0060659 | A1 | 3/2011 | King et al. |
| 2017/0031676 | A1 * | 2/2017 | Cecchetti .............. H04L 9/3236 |
| 2017/0286572 | A1 | 10/2017 | Hershey et al. |
| 2018/0210436 | A1 | 7/2018 | Burd et al. |
| 2019/0251575 | A1 | 8/2019 | Berti et al. |
| 2019/0287181 | A1 | 9/2019 | Lekas |
| 2019/0317935 | A1 | 10/2019 | Berti et al. |
| 2019/0333169 | A1 | 10/2019 | Povar et al. |
| 2019/0377904 | A1 | 12/2019 | Sinha et al. |
| 2020/0034766 | A1 | 1/2020 | Borges |

OTHER PUBLICATIONS

Penzes, Balint, "Blockchain Technology in the Construction Industry: Digital Transformation for High Productivity", Dec. 2018; Ice: Institution of Civil Engineers, 52 pages. (Year: 2018).

Miskins, Carlos, "Digitizing the Construction Sector Using Digital Twin Technology Simulations", Dec. 2018, https://www.challenge.org/insights/digital-twin-in-construction/, 8 Pages.

Verma, Urvashi, "What Are Digital Twins in Smart Buildings?", Oct. 31, 2018, https://inbuildingtech.com/bms/Jigital-twin-commercial-office-building/, 9 Pages.

Ghanem, Amine et al., "A Case Study for Improving Construction Project Management", 51st ASC Annual International Conference Proceedings, 9 pages (Year: 2015).

Barista, David, "'BIM for all' platform pays off for contractor", https://www.bdcnetwork.com/bim-all-platform-pays-contractor, Aug. 13, 2020; 12 pages.

* cited by examiner

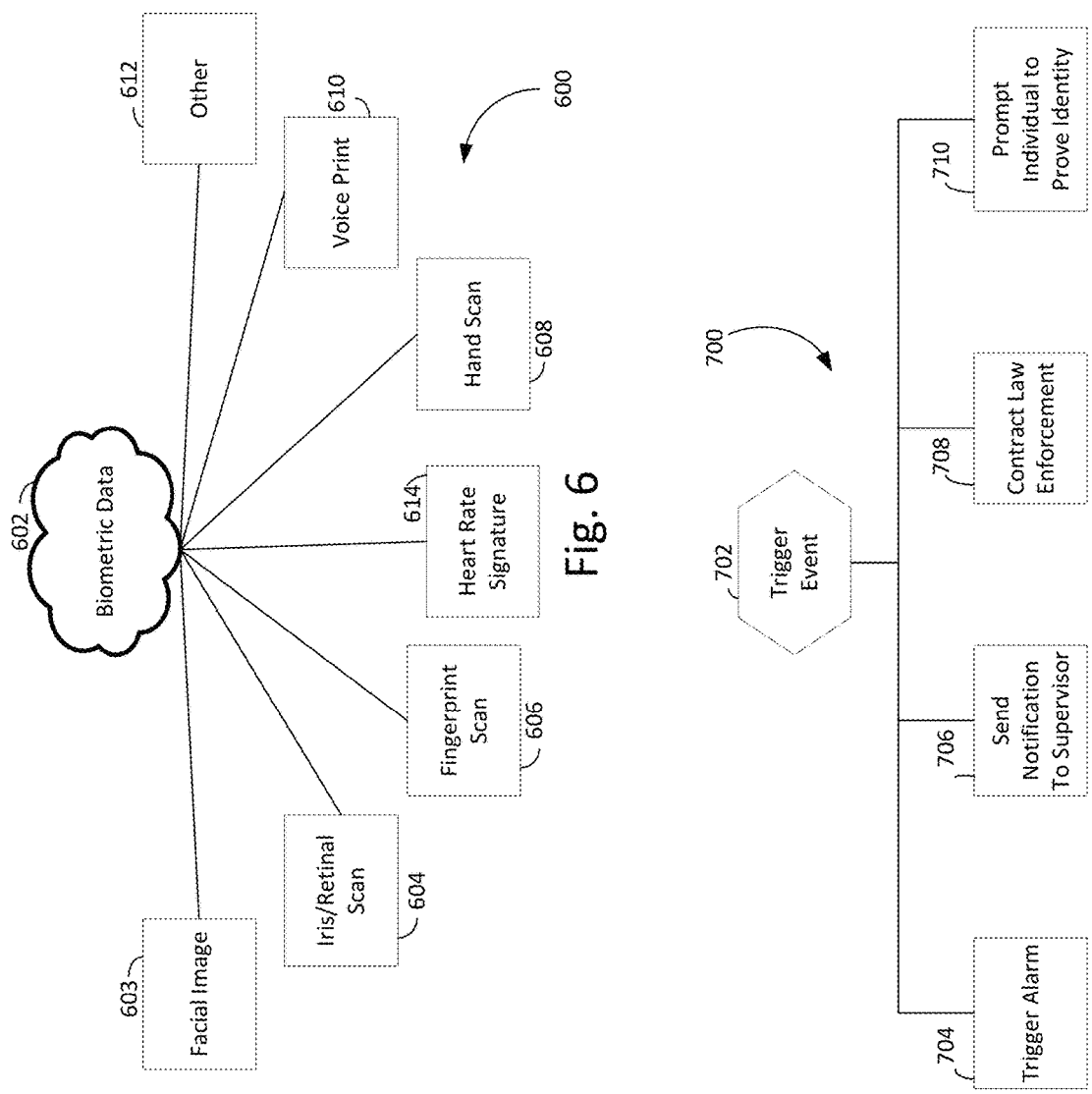

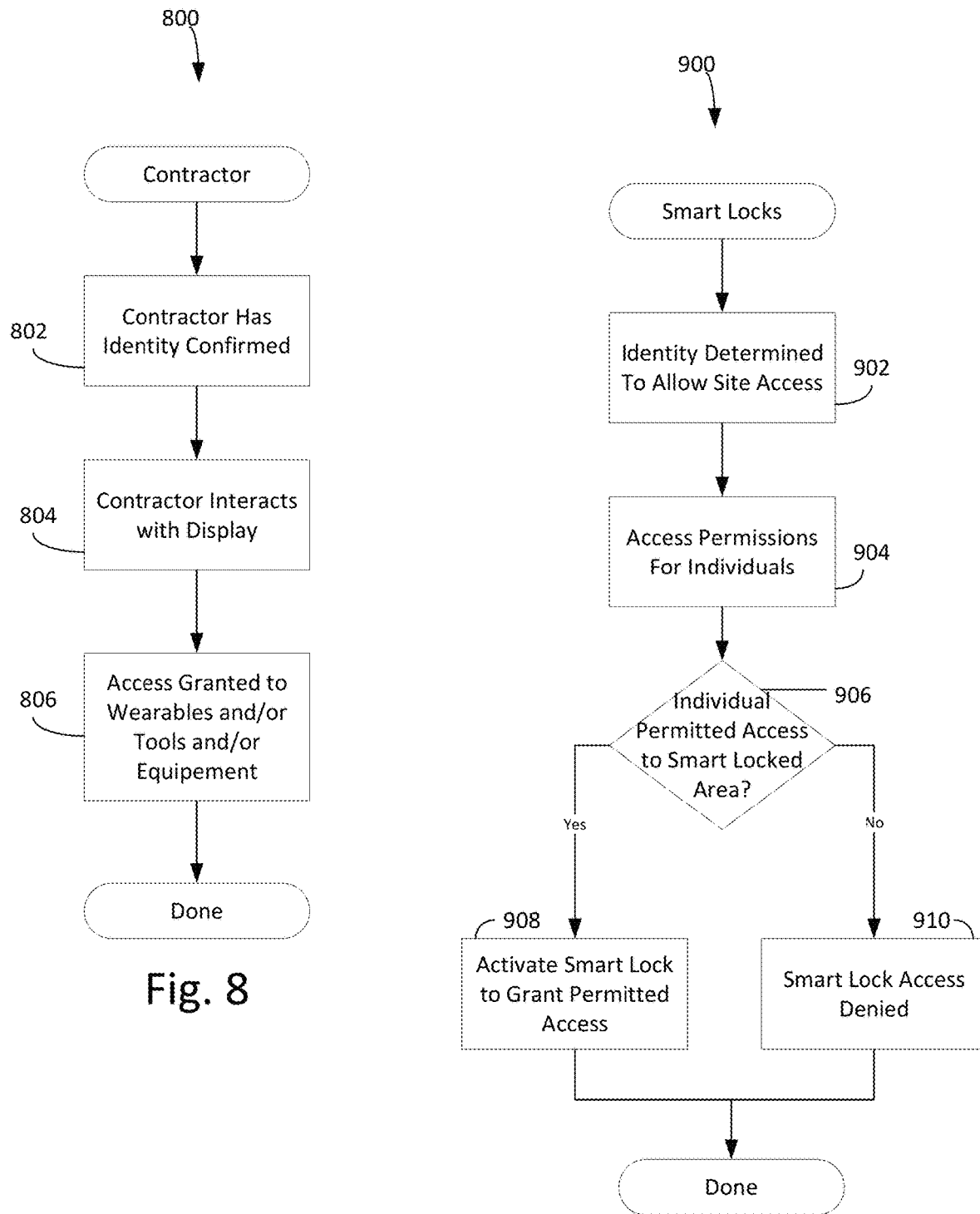

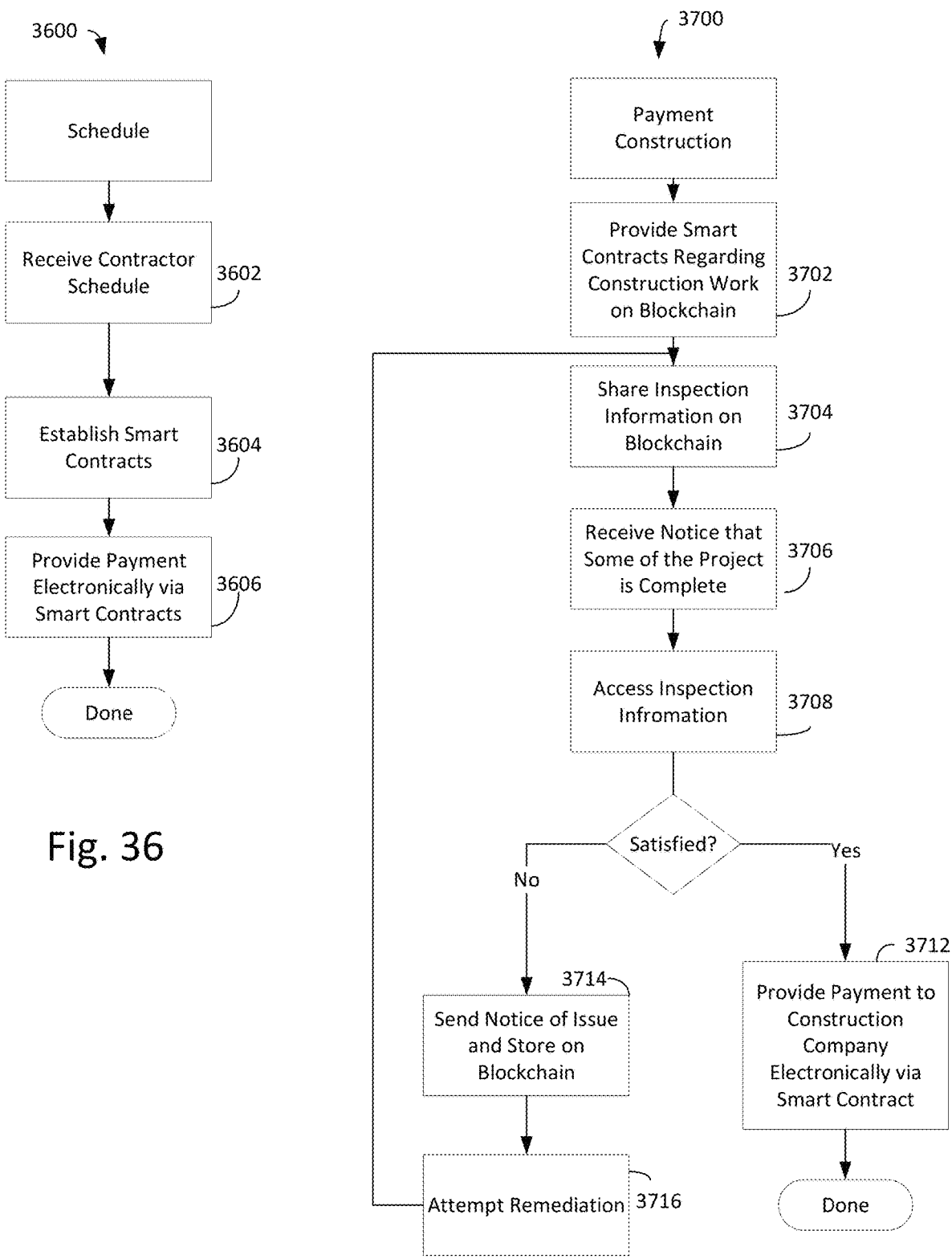

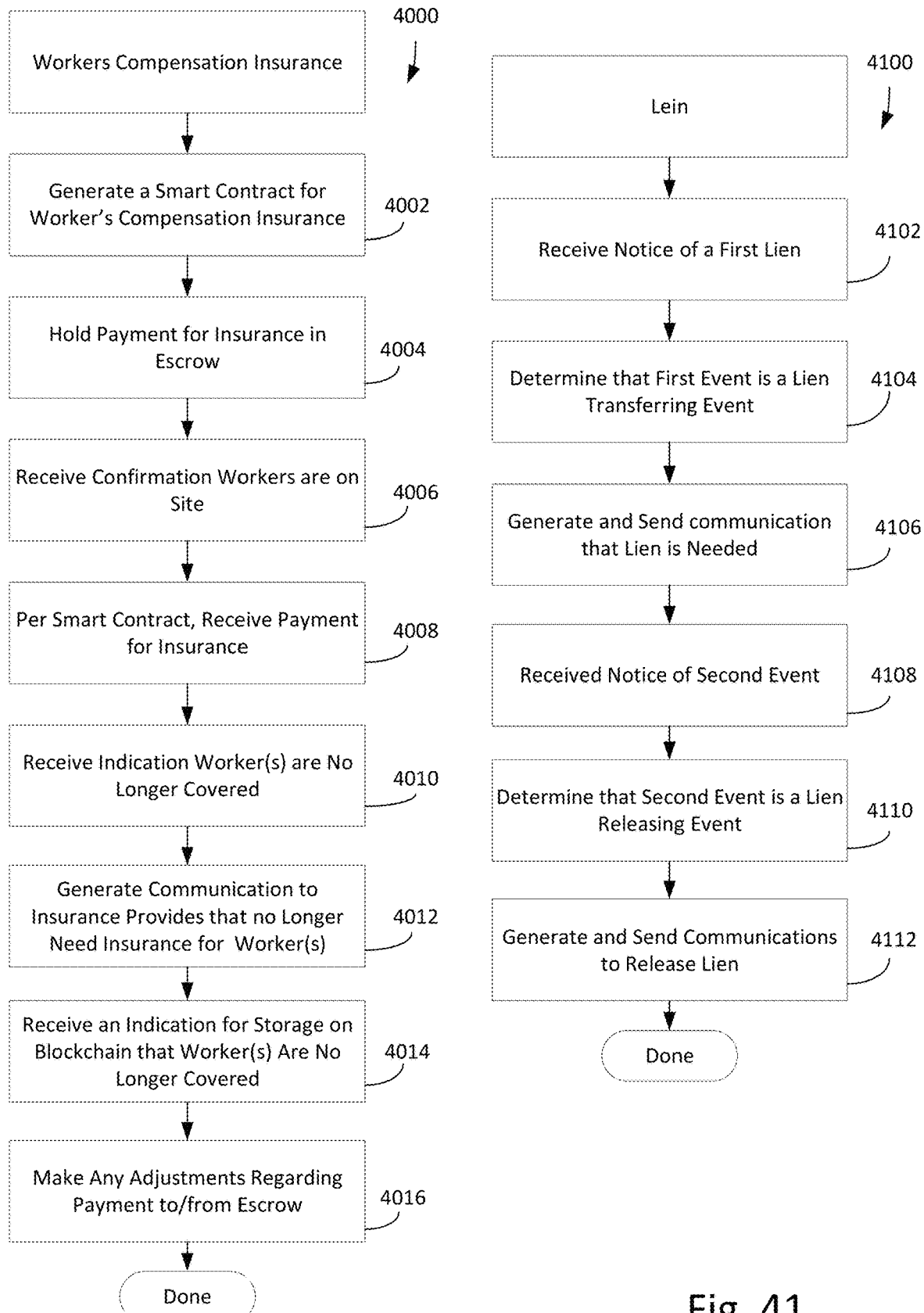

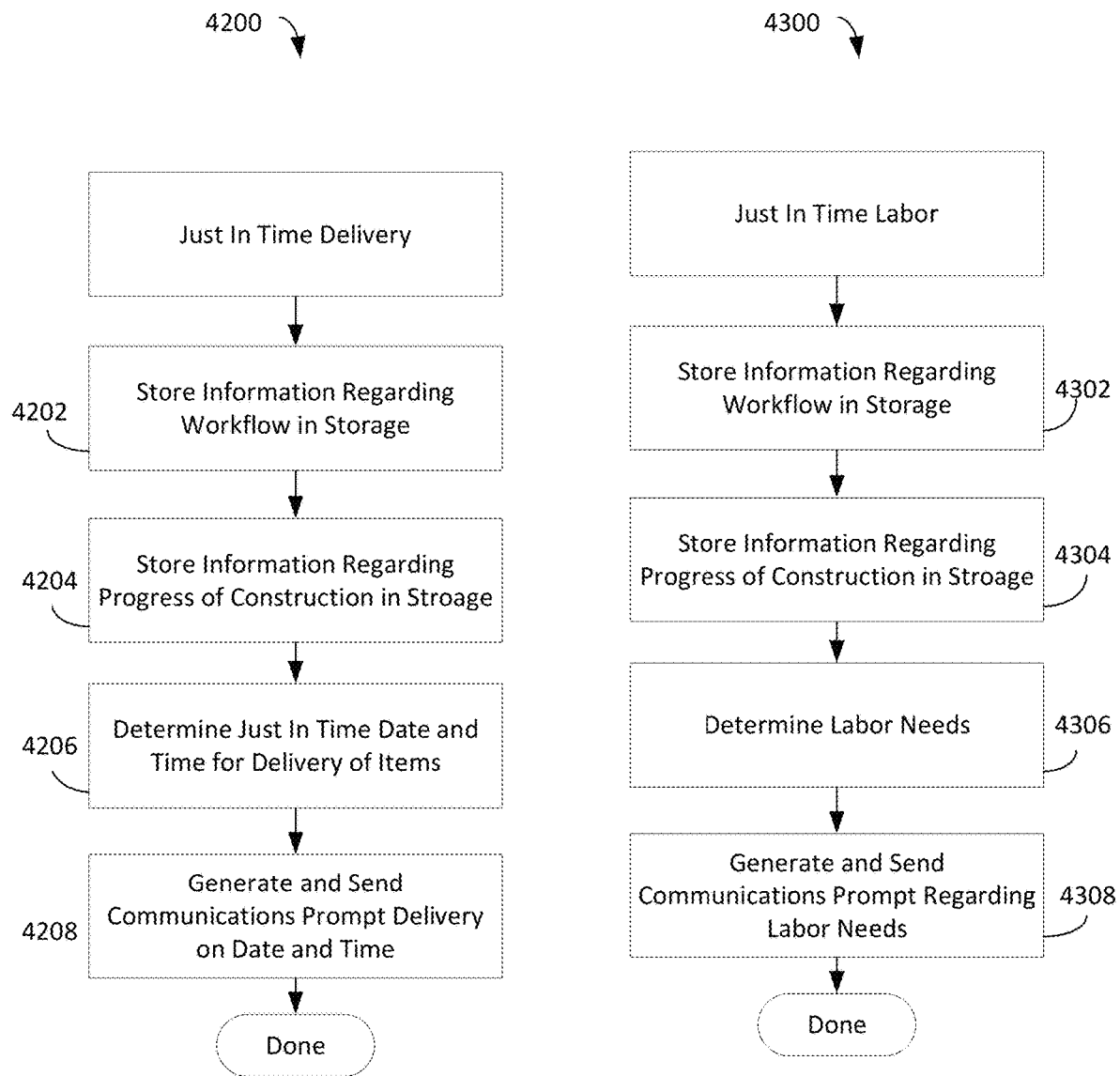

SYSTEM FOR MANAGEMENT OF INSURANCE RISK AND INSURANCE EVENTS

RELATED APPLICATIONS

The present application is a continuation in part of U.S. patent application Ser. No. 16/994,585 filed Aug. 15, 2020 entitled System For Management Of Verification Of Project Commencement and Completion, which in turn is a continuation in part of U.S. patent application Ser. No. 16/991,916 entitled "System For Management Of Warranty Information For Projects And Materials" filed on Aug. 12, 2020 which in turn is a continuation in part of U.S. patent application Ser. No. 16/876,080 entitles "Digital Asset System For Management Of Projects And Materials", filed May 17, 2020 which in turn is a continuation in part of U.S. patent application Ser. No. 16/810,782, entitled "System For Management And Verification of Code Compliance," filed on Mar. 5, 2020 which in turn is a continuation in part of U.S. patent application Ser. No. 16/410,634, entitled "Use of A Persistent Storage Reference Construction Metadata and to Use Smart Contracts for a Construction Project," filed on Jul. 12, 2019, U.S. patent application Ser. No. 16/510,642 entitled "Use of a Blockchain-Based Distributed Ledger and Smart Contracts for a Construction Project" filed on Jul. 12, 2019 both of which are continuations of U.S. patent application Ser. No. 16/452,076, entitled "Site Super System For Construction Sites", filed Jun. 25, 2019 which all are incorporated reference.

BACKGROUND

1) Field of the System

This system is directed to a system tied to a construction site, provides for multiple party information verifications, and creates an immutable record for management and verification of insurance coverage and compliance associated with workers, constructions material and the construction process and stores the insurance information on an immutable and/or distributed ledger.

2) Background

For any construction project, there is a systematic and logical workflow that increases the success of the project. Workers, materials and the other individuals that are included in a successful project include approved architectural design, approved construction materials, licensed, legal, qualified, and experienced workers or laborers, permits, insurance, financing, and inspections. Architectural designs can include a bill of materials representing construction materials to be used for the construction project that can be sent to suppliers or manufacturers so that the cost of the bill or materials is known prior to ordering the materials and finalizing the architectural plans. Each component of the materials can include a warranty that is from the manufacturer, distributed, installer or any combination. The requirements for a warranty to remain in place can include requirements such as compliance with installation processes, environmental conditions, use of licensed workers, use of qualified and experienced workers and any combination.

One disadvantage of the current construction process is the lack of accountability, verification and reliability of information related to the materials used, tasks performed and workers that perform tasks. These items can affect the validity of insurance, increase risks and claims and therefore increase premiums. Further, the inability to verify correct materials, installation, workers and other factors can results in loss, mistakes, injury and insurance claims. This weakness in the current process and system negatively impact the insurance process, coverage, risks and costs in general.

Building codes also impact the construction site and are a set of rules that specify the standards for a construction project. Codes impact the architectural design, constructions materials, worker's license and experience the construction process. A building code may require that building materials be installed in accordance with manufacturer's specifications and warranty regulations. Failure to follow these requirements can results in insurance companies failing or cancelling coverage. This requires management and verification of the materials to ensure regulatory code compliance and proper installation according to the specifications. Tracking this requirement can be difficult because the materials can be hidden from view or otherwise inaccessible. The issue with the current systems is that there is no established verifications process to ensure that the materials actually used are the ones that were designated in the codes or architectural design. While a building inspection is designed to reduce this risk, inspections of components during and after construction cannot be properly verified as they can be obscured. For example, plumbing will be covered by walls, fixtures, floors and the like and inspection can be impossible.

It would be an advantage to have a system that can receive designs from architects that are approved for construction and confirm that the materials specified are used and installed by the appropriate workers and under the proper conditions. It would be an advantage to have a system that can determine if insurance requirements are followed during the construction process and provide notifications if there is a risk of invading insurance coverage. It would be an advantage to have a system that can receive claim information, such as injuries, at the construction site locations and associate the claim with the injury in real time, communications with a claims agent and suggest medical attention or other remedial measure as needed while the subject of the claim, an individual or material is at the construction site.

Verification that propose worker are authorized, proper material are used and installation procedures are followed is important because suppliers and contractors are known to substitute lesser quality materials, out of code materials, unlicensed or unauthorized workers, or take short cuts for financial reasons. Further, without third party verifications, inspectors can provide false or misleading information to sign off on a project when in fact the inspection preformed and that recorded are not consistent. When an inspection is preformed, the record of the inspection is not consistently maintained. Recordation ranges from physical forms to smart phone images to proprietary inspection system such as a computerized system offered by Inspection Support Network®. The data is stored and maintained by the system provider so that data security is dependent upon the system provider. It would be advantageous to have a permanent verified record of code compliance that can be referenced by third parties prior, during and after commencement of the construction project and for future verification of aspects of the project.

There have been since attempts to improve the construction process such as U.S. Pat. No. 7,898,403 that is directed to a method and system for detecting construction equipment process failures. A database is populated from information from a third-party source and a process failure report is provided for processes that are outside a norm assigned to the construction equipment asset. U.S. Pat. No. 7,031,930 is directed to a method and system for managing complex construction projects by monitoring subcontractors in real time, against a system after commencement of the project. U.S. Pat. No. 8,004,397 is directed to a mountable reporting source comprising a controller coupled with an interrogating component configured for automatically receiving an identifier which is unique to an asset having a position determining component. Again, this is directed to the construction process itself, not management and verification of code compliance.

To ensure that proper materials, installation, and workers are used, verifications of materials, confirmation of deliveries at construction sites, and obtaining sign offs are beneficial. Further, deliveries may be made regardless of weather conditions, resulting in some materials being subject to rain and other weather conditions that may negatively affect the materials that are delivered. This can result in legacy issues for warranties and quality. At large sites, errors may occur with deliveries to the wrong location or wrong contractor as different trades may use common materials. When materials are delivered, installed, or otherwise used in weather conditions that are contrary to the manufacturer specifications, significant damage and liability can be introduced to the construction project. For example, when moisture gets trapped behind the building material stucco, the moisture can produce "stucco tears," which result in discoloration of the stucco beneath windows or cause the formation of mold and mildew, which can escalate into an infestation of black mold. Manufacturers have certain requirements for stucco and its installation and can require certain humidity ranges and temperature ranges. It would be advantageous for a system to record the weather of the installation for this and other materials.

SUMMARY

In accordance with an exemplary embodiment, a computerized system for on-site management of accountability insurance risk and insurance events is provided comprising: a kiosk having a kiosk computer readable medium uniquely associated with a construction site and in communication with a distributed ledger; a sensor in communications with the kiosk for detecting the presence of workers at the constrictions site, materials at the construction site, events and conditions occurring at the construction site; a set of non-transitory computer readable instructions included in the kiosk computer readable medium for: for each worker present at the construction site, determining an arrival time, a departure time, an amount of time worked and worker class, identifying a set of construction materials delivered to the construction site, detecting an installation action performed by a worker when installing the set of construction materials, detecting an insurance event, identifying a set of environmental conditions associated with the insurance event, associating the insurance event with the environmental conditions, creating an insurance record according to the insurance event, and transmitting the insurance record to a third party computer device.

The computerized system can include a unique identifier taken from the group of a RFID, wireless signal, a digital identifier, an alphanumeric character, a graphic or any combination thereof. The insurance event can be a material loss according to a material identifier associated with a construction material. The set of non-transitory computer readable instructions include instructions for detecting a set of material loss circumstances and appending the insurance record with the set of material loss circumstances. The set of non-transitory computer readable instructions can include instructions for detecting an installation deviation representing a deviation to an installation instruction included in a building information model stored on the kiosk, detecting a set of installation deviation circumstances, appending the insurance record with the set of installation deviation circumstances. A drone having drone sensors can be included and the set of non-transitory computer readable instructions can include instructions for detecting the set of installation deviation circumstances using the drone. The set of non-transitory computer readable instructions can include instructions for assigning an equipment to at least one worker, determining if the equipment is removed from the construction site and appending the insurance record if the equipment is removed from the construction site. The insurance event can be a worker related event. The set of non-transitory computer readable instructions can include instructions for detecting a set of worker injury circumstances associated with the worker related event and appending the insurance record with the set of worker injury circumstances. The set of non-transitory computer readable instructions can include instructions for receiving an insurance claim associated with the worker injury and determining if the insurance claims is consistent with the set of worker injury circumstances. The set of non-transitory computer readable instructions can include instructions for receiving a set of worker coverage information from an insurance computer system and determining if the worker coverage information is consistent with the set of workers located at the construction site. The set of non-transitory computer readable instructions can include instructions for determining is insurance coverage is inconsistent with the insurance claim made in response to an insurance event. The set of non-transitory computer readable instructions can include instructions for determining if the insurance event occurred within a construction site boundary associated with the construction site. The set of non-transitory computer readable instructions can include instructions for establishing a communications session with an insurance representative when an insurance event is detected. The set of non-transitory computer readable instructions can include instructions for transmitting a notification of the insurance event to a third-party computer device. The set of non-transitory computer readable instructions can include instructions for establishing a communications session with an event responder. The event responder can be associated with a communications system taken from the group consisting of a medical provider, first responder, Insurance representative, on-site manager or supervisor, off-site manager or supervisor, insurance entity, financial entity, owner, or any combination thereof.

The insurance event can represent a construction material being removed from the construction site and the set of non-transitory computer readable instructions include instructions for detecting when the construction material is removed from the construction site. The set of non-transitory computer readable instructions can include instructions detecting an installation action performed by a worker when installing the set of construction materials, The sensor can be a video capture device and the set of non-transitory computer readable instructions include instructions recording video information upon the occurrence of an insurance event. A weather station can be in communications with the kiosk configured to detect an actual installation condition and the set of non-transitory computer readable instructions include instructions for determining if the actual installation condition is outside the a recommended installation condition included in a set of installation instructions. The system can include a biometric sensor associated with a worker; wherein the insurance event is an injury to a worker; and, the set of non-transitory computer readable instructions include instructions for detecting a biometric value outside an acceptable biometric value range associated with the worker.

The system can include a video capture device; and the set of non-transitory computer readable instructions include instructions for confirming a worker has safety equipment properly installed according to video verification from the video capture device.

A biometric signature can be associated with a worker and the set of non-transitory computer readable instructions include instructions for confirming a worker has safety equipment properly installed according to the biometric signature and video capture device.

A computerized system for on-site management of accountability insurance risk and insurance events comprising: a kiosk having a kiosk computer readable medium uniquely associated with a construction site and in communication with a distributed ledger; an insurance information received from an insurance provider computer system representing insurance coverage requirements for loss risks taken from the group consisting of workers compensation, property casualty loss, construction risk, general liability, health, life or accidental death or any combination thereof; a set of non-transitory computer readable instructions included in the kiosk computer readable medium for: detecting an insurance loss, determining if the insurance loss occurred within a coverage period, detecting a set of loss circumstances, creating a loss record according to the set of loss circumstances, and, storing the loss record on the distributed ledger. The set of non-transitory computer readable instructions can include instructions for determining if an insurance exclusion applies to the insurance loss according to the set of loss circumstances. The system can include a power source for equipment included in the kiosk; wherein the insurance loss is a personal injury, and, the set of non-transitory computer readable instructions include instructions for restricting power to the power source if the insurance loss is detected. The system can include a warning indicator included in the kiosk; and, the set of non-transitory computer readable instructions include instructions for actuating the warning indicator if the insurance loss is detected. The system can include a warning indicator included in the kiosk; and, the set of non-transitory computer readable instructions include instructions for actuating the warning indicator if a predetermined risk factor is met.

A computerized system for on-site management of accountability insurance risk and insurance events comprising: a kiosk having a kiosk computer readable medium uniquely associated with a construction site; a biometric sensor associated with a worker and in communications with the kiosk; a set of non-transitory computer readable instructions included in the kiosk computer readable medium for: detecting an insurance event according to the biometric sensor, and, creating an insurance record according to the insurance event and transmitting the insurance record to an insurance computer system. The set of non-transitory computer readable instructions can include instructions for detecting a biometric value outside an acceptable biometric value range associated with the worker. A computerized system for on-site management of accountability insurance risk and insurance events comprising: a kiosk having a kiosk computer readable medium uniquely associated with a construction site; a sensor in communications with the kiosk for detecting the arrival of a construction material at the construction site and detecting an installation action performed by a worker when installing the construction material; a set of non-transitory computer readable instructions included in the kiosk computer readable medium for: determining when the construction material arrives as the constriction construction site, retrieving the value from a supplier computer system, creating a material arrival record according to the determination that the construction material arrival and replacement cost. The set of non-transitory computer readable instructions can include instructions for transmitting the increased replacement costs to an insurance computer system. The value can be the replacement cost, repair cost, market value, or other amount representing what the insurance policy will pay in the event of a loss.

BRIEF DESCRIPTION OF THE DRAWINGS

FIG. 6 shows various types of biometric data that may be gathered.

FIG. 7 shows types of events that may be triggered.

FIG. 8 shows a flowchart illustrating aspects of the system.

FIG. 9 shows a flowchart illustrating aspects of the system.

FIGS. 36-43 shows a flowchart of steps performed by the system.

DETAILED DESCRIPTION

Figure 1B:
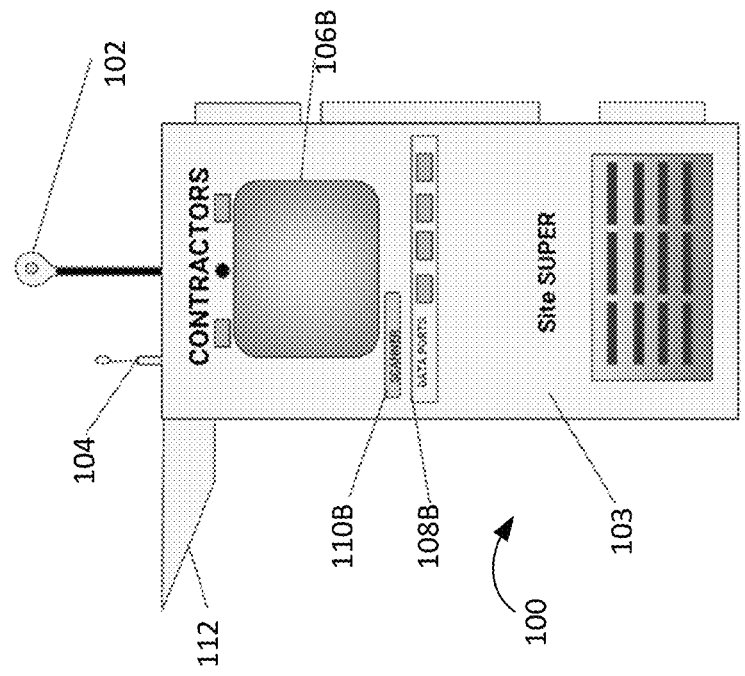
FIGS. 1A-1F shown various side views of aspects of the system.

Systems at nearby construction sites may be interconnected using image capture devices, such as still cameras or video cameras, to provide security not only to the site on which it is stationed, but nearby sites as well. The processing of images from the multiple interconnected systems may be performed via processing logic to identify security issues.

A system utilizing biometrics for verification of actual workers on the construction site to correspond with professional licenses and work certifications for verified payroll and insurance coverage would optimize processes and ensure coverage. Onsite verification of processes, inspections, completions and deliveries with automated adjustments and notifications with confirmation would ensure increased productivity, especially if accessible in real time at the construction site. Real time construction plans with corresponding training and construction manuals would improve quality control and efficiency but rarely exist.

Automated verification of quantities, quality, and correct product deliveries along with after delivery tracking of materials with accountability is seldom used. Designated delivery areas with geofenced control and tracking of materials once delivered would help prevent loss. Confirmation of products integrated at a construction site provides transparency regarding sourcing, warranties, as well as future reference during the structure and individual products life of use.

The system seeks to identify all individuals entering or leaving the construction site and persistently records this information in a storage, such as in a database. Such records may be useful in a number of different contexts. The biometric-based identification device may be a camera or other image capture device. Facial recognition may be performed on the captured facial image to attempt to identify the individual. Alternative biometric-based identification devices, such as voice recognition systems, retinal scans, fingerprint scanners, hand scanners, voice print devices and the like may be utilized in the alternative or in addition to other biometric devices. As a last resort, the computing logic may allow authorized individuals to manually enter the presence of another authorized individual.

The present system allows, in real time, the determination of what materials are delivered to the construction site which allows for the insurance coverage to increase as additional materials are added. Further, as tasks are completed, the insurance coverage can be increased according to the value of the completed projects. This is an improvement over the current methods which use a arbitrary determination of the value (e.g. some percentage) without consideration of the actual value of the materials of the value of the completed work. Further, such insurance coverage ad workers compensation can be determined based upon the actual workers at the construction site and not rely upon "reported" workers. The benefits of the current system improve cash flow and risk management by basing insurance premiums and coverage on actual risk and not actuarial risk. Actuarial risk can refer to the assumptions that actuaries use in insurance models to price specific insurance policies. Actuarial risk can be inaccurate or simply wrong as the assumptions and the data from the insurance client or potential insurance client is not verified. Possible assumptions resulting in incorrect assumptions include the frequency of losses, the severity of losses, and the correlation of losses between contracts. The data captured by the system can be provided to the insurance company in real time.

The system may record the date and time of events such as the arrival and departure of individuals, supplies, third parties, inspections, and the like to and from the construction site. The system may also record the date and current weather conditions. The weather information may be used to modify the schedule for workers so that workers are not working during inclement weather and to record the weather conditions at the time that the worker worked, and materials are delivered and installed. Additionally, the processing logic may prevent work from being performed if said work would violate manufacturer guidelines for installation/application. The recorded information may also be useful in providing or disproving insurance claims or worker's compensation claims and be useful to confirm installations or adherence to manufacturer specifications related to temperature or weather-related conditions.

If the system determines that an unidentified individual attempted to enter the construction site, the system may take the appropriate responses, such as sending notifications, triggering alarms, and/or contacting law enforcement authorities or security. The decision as to the appropriate response may be determined by, the date, the time current weather conditions, or related factor.

The system may also control access to tools, equipment, materials, and areas of the construction site. As to tools, equipment and materials, the system may confirm the identity of an individual and grant access to certain tools and equipment using smart locks and/or other technology. The system may limit the dates and duration of access to the tools/equipment such that the tools/equipment must be returned within the specified date/time window. An onsite scanner can be used to identify tools, equipment, materials, and areas of the construction site such as by using barcode or other identifying information to track these items, associate them with ah worker or area of the construction site.

The smart locks may also be used to limit access to certain portions of the project under construction. An individual's right to a portion of the construction site may be dictated by permissions that are stored through each party involved in the construction process. This may eliminate keyed entry during the process and provide further verifications of individual or group access.

The individuals on the construction site may be prompted to wear certain wearables that provide useful information to the system. For instance, individuals may be prompted to wear location tracking devices, such as GPS devices, Bluetooth, radio frequency identification (RFID) devices, ultra-high frequency (UHF) and/or beacon-based devices. The use of the wearables helps to perform geofencing within the construction site. The location tracking provided by the wearable helps the system to monitor the location of individuals on the construction site on an ongoing basis. The permissions may define what portions of the construction site an individual may access. Ongoing monitoring may indicate that an individual is attempting to enter a location where the individual is not permitted. This may trigger a response as described herein. A signal may be sent to the vest or wearable to trigger a visual or audio cue that the individual is not in a permitted area. In addition, individuals may be requested to wear wearables that track biometric information, such as heart rate, body temperature, respiration rate and blood pressure. This information may be tracked and stored on an ongoing basis. When the biometric data gathered from these wearables are outside an acceptable range, potentially indicating physical danger or injury, appropriate response actions may be taken such as notifying the individual, notifying a supervisor, and/or contacting medical personnel. Collected data may be used to verify a multitude of factors such as reported accidents, incidents of theft, hours worked, and the like. In the event that an accident occurs, the system can record information about the accident such as the worker involved, the equipment being used, physical location, other worker in the area, video capture from camera in the area, material involved, tools and equipment involved and record the information for reporting and future study.

The system may track materials. When a delivery is made, the delivery person may enter delivery notes and the delivered materials may be scanned or read to confirm the quantity and nature of what has been delivered and current weather conditions. The system can record weather information at the location and time where the materials are received, stored, and installed. Recording weather information at the construction site allows for autonomous confirmation of weather conditions that do not rely solely on third party sources. The system may track the movement of materials, tools, and equipment at the construction site. Scanning technology such as RFID readers, UHF readers and/or the like may be utilized to assist the location tracking for tools, equipment, and materials. The tracking of materials helps reduce the risk of theft. For example, the tracking solution may indicate instances of possible theft, such as when the materials are leaving the construction site when the removal of the materials is not appropriate.

The system may allow for the establishment of one or more geofenced delivery zone areas. These areas could be monitored and established with additional access restrictions to individuals to further prevent loss or damage of materials. The system can determine the area where the materials are stored to assist in insuring that the materials are received and stored in compliance with the warranty specifications for the materials.

The system may control access to power by individuals of the construction site. The system may provide several power outlets and may grant access to the power outlets as warranted. The use of power may be recorded by the system. Different levels of voltage may be provided as required. The system can also restrict power usage during predetermined events including warranty confirmatory, safety situations and the like.

The system, including the kiosk, may also interface with the inspectors such that an inspector may enter notes and related details of an inspection. The system may allow the inspector to capture images of notes, forms, and the like using various solutions. The system can receive a set of internal inspection information entered into the kiosk from an internal inspector representing an internal physical inspection of the construction project at predetermined stages of the construction project. As component of the construction project are completed, an internal inspector can provide inspection information representing the component or stage of the construction project has been properly completed. This allows for inspections to be performed and recorded on the distributed ledger prior and any correction, if needed, to be performed prior to an inspection. The system can also receive a set of external inspection information from an external inspector and an external inspection computer device representing a third-party physical inspection of the construction project at predetermined stages of the construction project. Based upon the internal inspection, external inspection or both, a certificate of inspection can be created and stored on the distributed ledger.

Exemplary embodiments may reference a record of a construction project on persistent storage. The process of maintaining the record for the construction project may begin by the development of a Building Information Model (BIM) that contains 3D plans for the construction with full details. Based on the BIM, a Bill of Materials (BOM) may be determined. The BOM may contain a complete itemization of materials needed for the construction project. The BOM includes information such as make, model, quantity, warranty information, hazardous material information or other safety details. The BOM may be updated as actual materials arrive to the site that includes serial numbers, bar codes, QR codes, RFID values or other component or product identifications.

Materials arriving to the site may be recorded, as well as the BIM and BOM, on the persistent storage.

The exemplary embodiments may receive or determine a construction schedule that contains full project details and sequencing, including the specification of dependencies. Smart contracts may be provided that use the persistent storage for each step or task of the construction schedule. This information and the schedule may be augmented with worker or employee lists for each task. The smart contracts may set forth acceptance or inspection requirements for confirmation of completion and payment.

The exemplary embodiments may confirm conditions at the construction site and may record weather conditions at the time certain tasks are started, stopped, and/or marked as complete. The exemplary embodiments may record the weather conditions related to the materials on site.

The exemplary embodiments may build a complete record of plans, the actual "as built" including make, model, serial number, or other identification of for every component in the home resulting from the construction project. The record may include a complete record of who completed the work, who inspected the work and how the project was insured and funded. This record may be updated as any property management adds information like maintenance requests, maintenance completions, utility usage, rental history, etc.

FIGS. 1A-1D illustrate an example of a system for an exemplary embodiment. In FIGS. 1A-1D, the system is implemented as a kiosk 100. The kiosk 100 may be located at a construction site and include a computer readable medium. One suitable approach is to pour a concrete slab and then position a kiosk on the slab in a secured manner. The kiosk can be physically associated with the construction site, virtually associated with eh construction site of both. The kiosk can removeable attached to the construction site so that it is stationary during a first construction project but can be moved to a second construction project once the first construction project is completed.

The kiosk can be physically associated with the construction site, virtually associated with the construction site of both. A unique identifier can be disposed at the construction site to uniquely identify the construction site. For example, a transmitter such as a RFID can be associated with the construction site by embedding it is a permanent fixture such as concrete slab, foundation, and the like. The kiosk can read the information from the unique identifier and therefore associate its location with the construction site. The unique identifier can also include an alpha, numeric of graphical information such as a number, letters, barcodes, QR code, physical or geographic coordinates (e.g. GPS coordinate) and the like. Each construction project can have a unique number and each construction site can have a unique number.

Figure 1A:
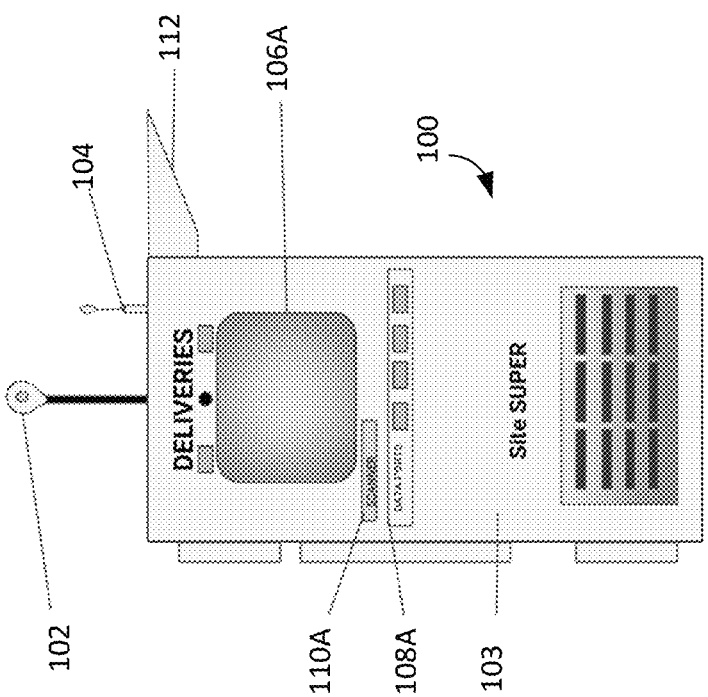

FIG. 1A shows a first side of the system kiosk 100. The kiosk 100 includes a camera 102 for obtaining images of individuals entering or leaving the construction site as well as images of individuals along a perimeter of the construction site. As will be explained in more detail below, the camera 102 may capture biometric images upon which biometric recognition may be performed. Multiple cameras may be placed on or around the kiosk 100. The cameras may have biometric recognition and motion detection capabilities. Kiosk 100 may include an addition to the camera 102 or instead of the camera 102, biometric-based identification devices that may be used to confirm the identity of individuals entering, leaving or on the perimeter of the construction site. The kiosk 100 may include an antenna 104 for communicating with a wireless network, such as a WiFi network, Bluetooth or a 4G/5G cellular network. The kiosk 100 may include a housing 103 made of suitable weather resistant material, appropriately sealed to protect the internal hardware. The kiosk 100 may include a display 106A, such as a touchscreen display, upon which information may be displayed and entered. The display 106A may include an integrated camera that may be used to capture images and that may be used in performing facial recognition of individuals. The display may also include or operatively associated with one or more integrated speakers for providing audio output, a microphone for receiving audio information to facilitate two-way communications to a remote location. The kiosk 100 may include a scanner 110A for scanning items, such as deliveries, as will be explained in more detail below. The scanner 110a may be, for example, a QR scanner, an Optical Character Recognition (OCR) or a bar code scanner 110A in some instances. The side of the kiosk 100 shown in FIG. 1A is intended to be used for deliveries and inspections. A delivery person may scan delivered items via the scanner 110A and may interface with the kiosk using the touch screen display 106A, as will be described below. An inspector may scan or take images of inspection documents via the scanner 110A or camera and may interface with the kiosk using the touch screen display 106A, as will be described below. In some alternative embodiments, there may be fewer sides in which to interact with the kiosk for all authorized personnel. An overhang 112 may be provided to assist in decreasing glare and protecting some of the items on the kiosk from the weather.

FIG. 1B depicts a side of the kiosk 100. This side also includes a touch screen display 106B as well as a scanner 110B. Display 106B may include or be operatively associated with an integrated camera for capturing images, speakers for providing audio output and a microphone to facilitate two-way communications with a remote location. Still further, this side of the kiosk 100 may include data ports 108B. This side of the kiosk is intended for use by contractors (e.g. workers and other construction related personnel). The kiosk 100 may be accessed to gain access to equipment, tools and to sign in or sign out when leaving or entering the construction site, as will be described below.

Figure 1D:
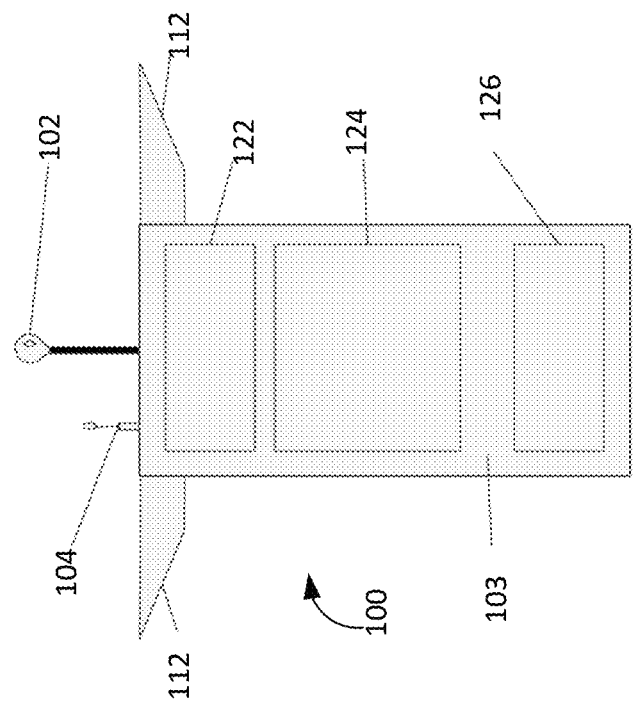
Figure 1C:
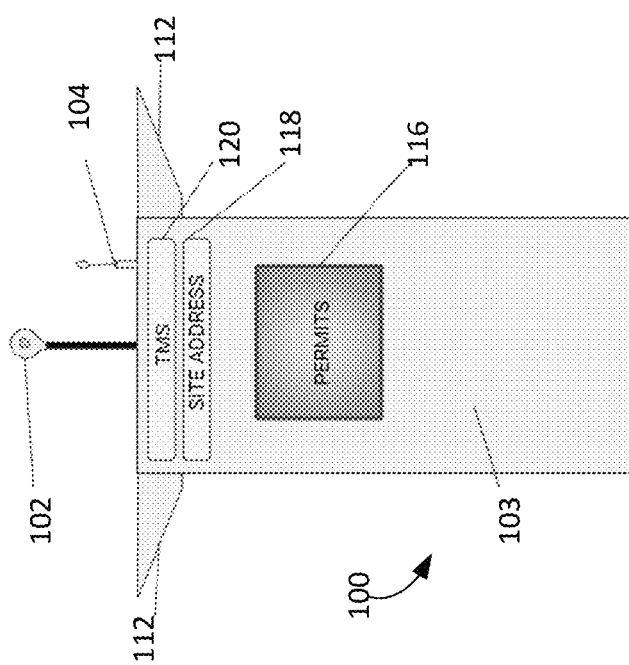

FIG. 1C shows a third side of the kiosk 100. This side has a location 116 in which permits (e.g. building permits, occupancy permits, and the like) may be displayed. In some alternative embodiments, the permits may assume electronic form so that a video display is provided in the area 116 of the kiosk 100. The tax map submap (TMS) number 120 for the construction site location may be displayed on the kiosk 100. In addition, the site address 118 may be displayed on the kiosk 100. The site address may refer to both the mailing address for the construction site and/or the GPS location.

FIG. 1D shows the final side of the kiosk 100. An access panel 122 may be provided to access a breaker box for the kiosk 100. An additional access panel 124 may also be provided to access internal components of the kiosk 100. Still further, access panel 126 may be provided to gain access to power plugs for providing power at the construction site. The access panel 126 may be under programmatic control in some instances to regulate access to the power plugs. If access is granted, the panel is unlocked, whereas if access is denied, the access panel 126 is locked. In some embodiments, access to the power supply may be controlled by controlling the flow of power to the power plugs under programmatic control. These control mechanisms may be used separately or in conjunction.

Figure 1F:
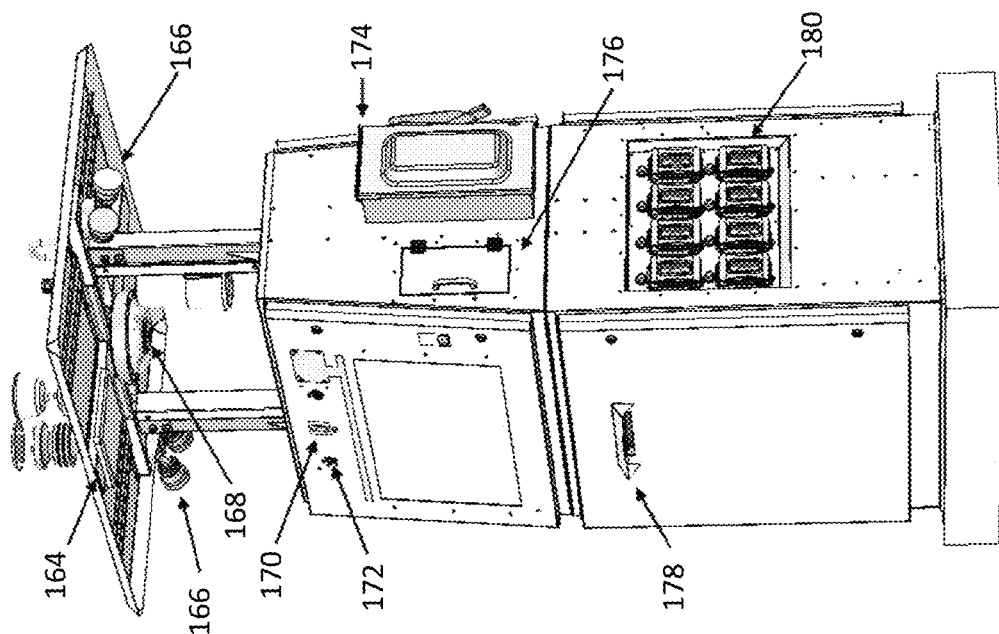
Figure 1E:
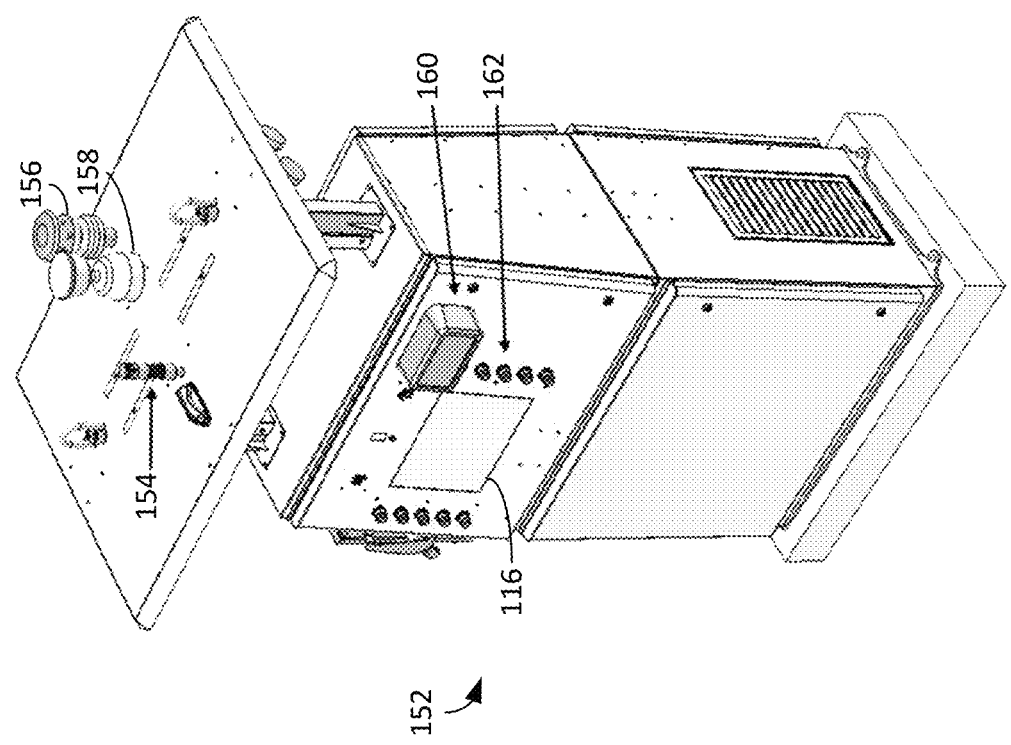

Referring to FIGS. 1E and 1F, the kiosk 152 can include a laborer side that is configured to be used by the labor at the construction site. The kiosk can include an alarm indicator 154 that can be actuated as described herein. The kiosk can include a weather station 156 and a rain collector 158. Biometric reader 160 can include an iris scanner, fingerprint scanner, palm print scanner or some combination. Display 116 can be proximity to input assemblies such as buttons 162. The kiosk can include a FR field receiver 164, lights 166 and camera 168. The camera can have a 360° field of view and include a wireless connection for transmitting images to remote computer device. The images can also be used for input to the kiosk including input allowing the kiosk to identify delivered materials. The kiosk can also include one or more second cameras 170 such as webcams disposed at various locations around the kiosk for capturing images. The lights can include motion activation and photoelectric activation. Speakers 172 can be included to provide audio information to a user, worker, inspector or other party using or near the kiosk. The audio information can include instructions, alarms, and the like. Power junction 174 can include a shut off switch that can be used in emergency and non-emergency situations. The kiosk can include a secondary power source, such as a battery, so that when the main power is shut off, an alarm can sound, notification send to a remote computer device of other indication that the kiosk has been powered down. The kiosk can include a hand scanner (not shown) that can be protected by a hand scanner access door 176. A document scanner 178 can be included in the kiosk for receiving physical documents, converting the physical document into a digital representation and storing the digital representation on the computer readable medium or the distributed ledger. The kiosk can include electrical outlets 180 for providing power to various tools and equipment at the construction site including recharging batteries. The kiosk can include a wired connection to remote computer devices of a transceiver to provide a wireless connection to remote computer devices.

Figure 1G:
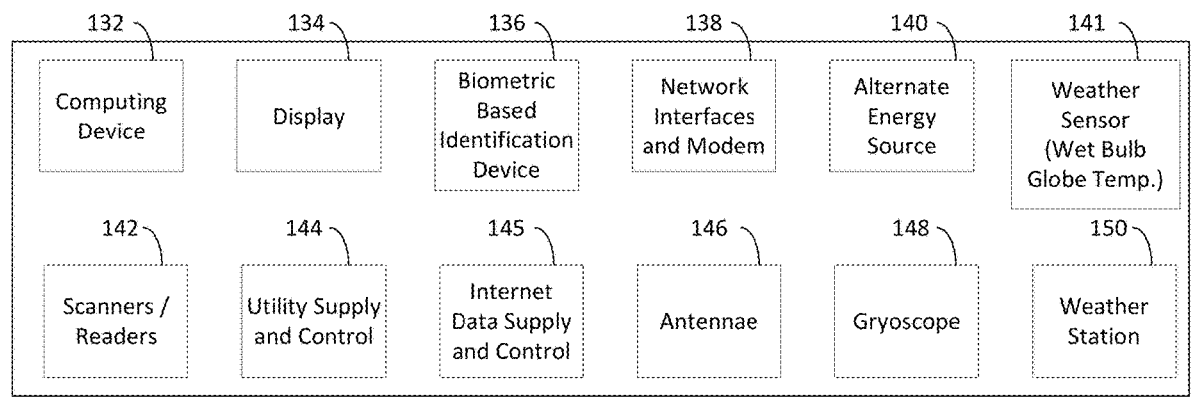
FIG. 1G is a block diagram of components of aspects of the system.

FIG. 1G depicts components that may be found in the site supervisor of exemplary embodiments even when not housed in a kiosk. The site supervisor may include a computing device 132. The computing device 132 may take many different forms indicating a desktop computing device, a laptop computing device, a mobile computing device, an embedded system, a smartphone, or the like. A display 134 may be integrated with the computing device 132 or as a separate device, such as a liquid crystal display (LCD) device, a light emitting diode (LED) display device or other types of display devices on which computer information may be displayed. One or more biometric-based identification devices 136 may be provided. As will be explained in more detail below, multiple biometric-based identification devices may be used. Network interfaces and a modem 138 may be provided. The network interfaces may interface the computing device 132 with a local area network or a wide area network. The network may be wired or wireless. A modem may be provided in order to communicate telephonically or over cable lines with remote computing devices.

The system 130 may be implemented in a distributed fashion and may include an alternative energy source 140. For example, solar panels, wind turbine(s), a battery or the like may be used. In a kiosk implementation, the alternative energy source may be physically affixed to the kiosk. For example, solar panels or a cable to a wind power source could be affixed to the kiosk. Alternatively, a power line leading to the alternative energy source may be connected to the kiosk to provide power for the kiosk.

The system 130 may include various scanners and readers 142, such as those described above relative to kiosk. The system 130 may include a utility supply and control 144 and a mechanism for turning the utilities, such as power, gas and/or water, on and off under a programmatic control. The system 130 may include an internet data supply control 145 and a mechanism for turning the access to this service on and off under a programmatic control. Programmatic control may be provided to grant or deny access to such resources. The system 130 may include an antenna 146 for wireless communications signals to receive and transmit. The system 130 may include a gyroscope 148 to monitor any moving of the system. The gyroscope 148 may indicate motion indicative of whether someone is trying to move or tilt the kiosk. Logic may be provided to send a notification in such an event where the gyroscope indicates substantial enough movement. The system 130 may include a weather station 150 to measure current weather conditions, such as temperature, air movement, humidity, precipitation, barometric pressure, direct sunlight, and the like. Input from the weather station 150 may be used to inform decision making by the system in some instances. Alternatively, the weather may be collected via software, such as from a weather service or other weather source. Similarly, the system 130 may include a weather sensor 141. The sensor can be a wet bulb globe temperature adapted to measure, among other things, heat stress in direct sunlight, which accounts for temperature, humidity, air movement (direction and speed), sun angle and cloud cover (solar radiation).

Figure 2A:
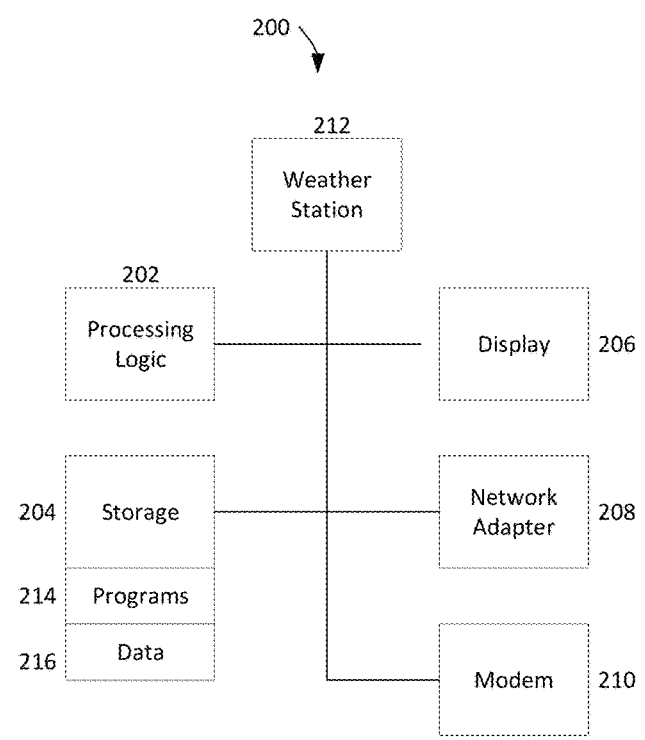
FIG. 2A is a block diagram of aspects of the system.

FIG. 2A shows an example of a computing device 200 for the system. The computing system may include processing logic 202, such as microprocessors, controllers, field programmable gate arrays (FPGA), application specific integrated circuits (ASICs) electronic circuitry, and other types of logic. The processing logic 202 performs the operations of the computing device 132. A storage device 204 may also be provided. Storage capability Storage device 204 may take various forms, including magnetic storage, optical storage, etc. Storage capability 204 may include computer-readable media, including removable computer readable media, such as disks, thumb drives and the like, or disk drives, solid state memory, random access memory (RAM), read only memory (ROM) and other types of storage. The computing device may include a display 206, such as an LCD display, an LED display or other types of display devices on which video information may be displayed. The computing device 200 may include a network adapter 208 for interfacing with networks and a modem 210 for communicating wirelessly, over telephone lines or cable lines with remote devices. The processing logic 202 may use information stored in the storage device 204. In particular, the processing logic 202 may execute programs 214 stored in the storage and may access and store data 216 relative to the storage device 204. The computational functionality of the system described herein may be realized by the processing logic 202 executing the programs 214.

Figure 2B:
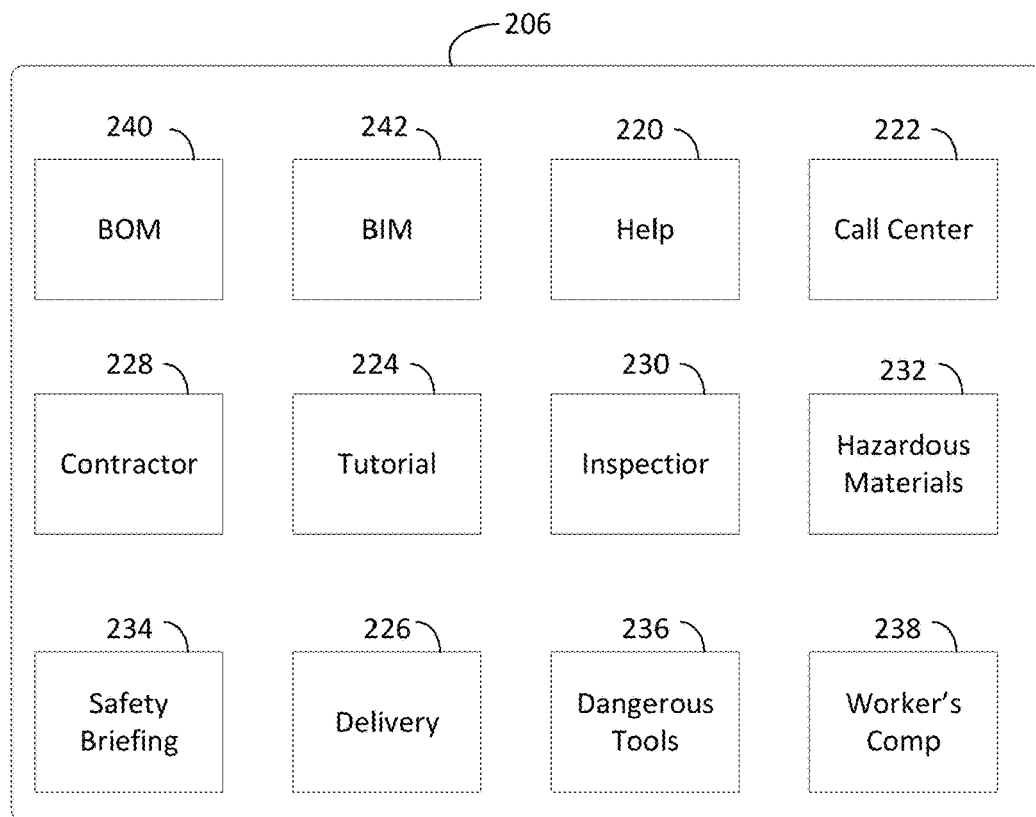
FIG. 2B shows aspects of a user interface.

FIG. 2B shows an example of a user interface on display 206, such as found in the kiosk 100. The user interface may include activatable elements. A user may depress these activatable elements or select these activatable elements using an input device, such as a mouse, keyboard, touchscreen or the like, to activate the components. The display 206 may include a help element 220 that may be activated to obtain help information regarding use of the kiosk. It may also contain real time construction plans. It may also include "how to" assistance including videos related to the various processes and tasks performed on the specific site. The user interface on the display 206 may also include a call center activatable element 222. Selection of the call center activatable element 222 may cause a call to be initiated with a call center so that the individual using the kiosk 100 may have a telephone and or video conference with personnel at the call center. The user interface on display 206 may also include a tutorial activatable element 224. Selection of the tutorial activatable element 224 causes a tutorial to be displayed to teach the individual about operation of the kiosk.

Figure 2C:
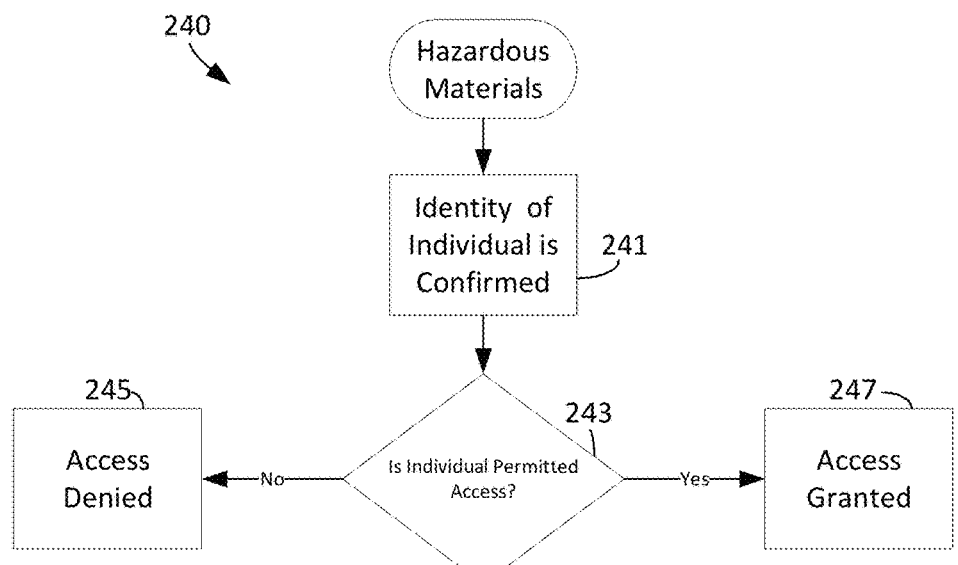
FIG. 2C shows a flowchart of aspects of the system.

A list of hazardous materials at the site may be activated by activating element 232. This list is updated as hazardous materials are delivered, removed or consumed. Access to hazardous materials may also be controlled via the system 130. FIG. 2C shows a flowchart 240 of steps that may be taken to control access to hazardous materials at the construction site. First, the identity of the individual is confirmed 241, such as described above using biometric identity verification. The permissions information is accessed to determine if the individual is to be granted access to the hazardous materials 243. If the permissions indicate that access is to be granted, access is granted 247. In contrast if the permissions indicate that access is not to be granted, then access is denied 245.

The user interface on display 206 (FIG. 2B) may also include a safety briefing activatable element 234. Activation of this element 234 results in a safety briefing being displayed on the display 206. The user interface on display 206 may include a dangerous tool activatable element 236. Activation of this element 236 causes the display of a list of dangerous tools on the construction site. An individual must have the proper authorization or certification to use such dangerous tools. The authorization or certification may be stored with the permissions.

Figure 2D:
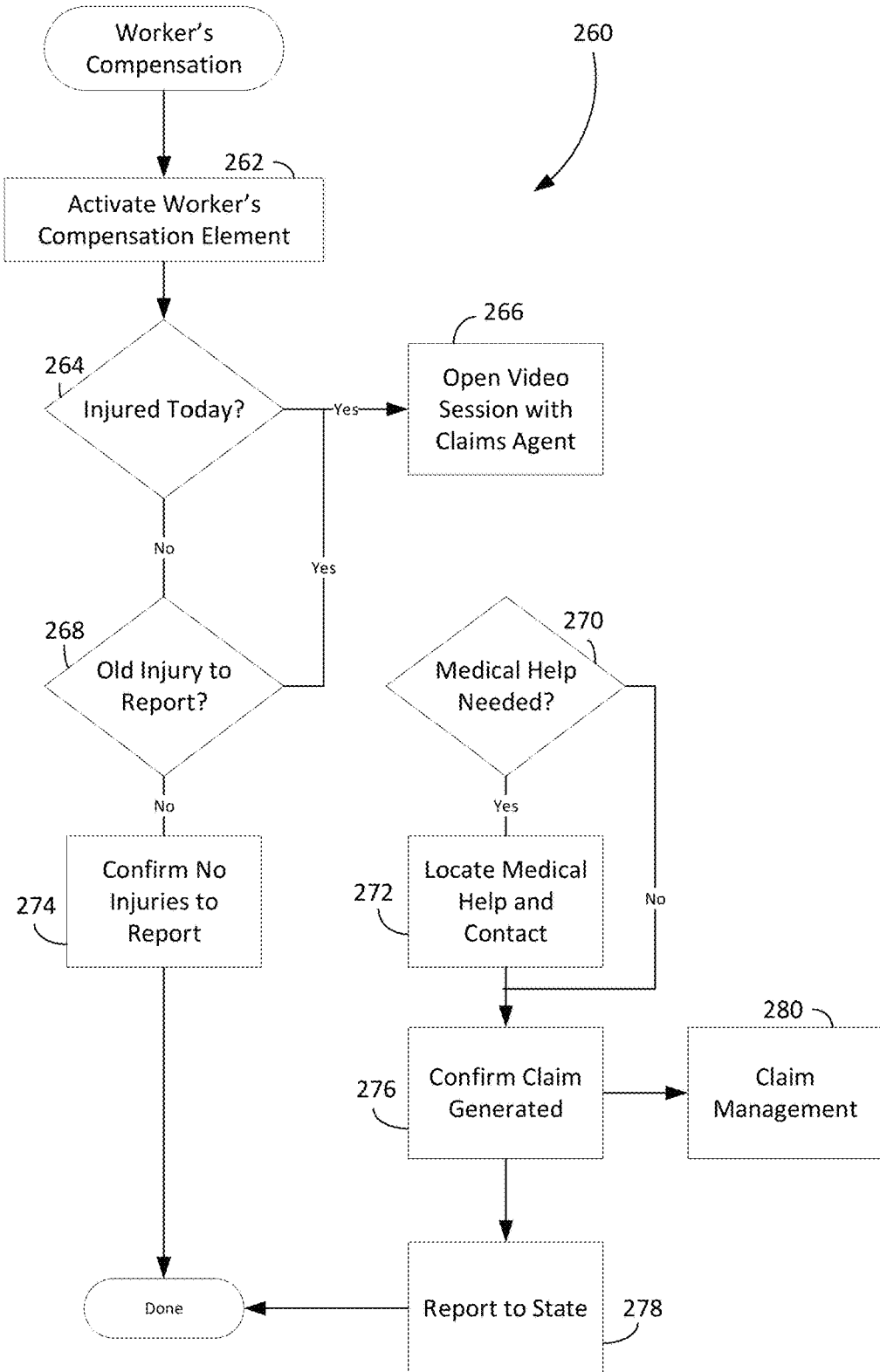
FIG. 2D shows a flowchart of aspects of the system.

The system 130 may include coding software which allows each tool to be assigned to authorized personnel. Utilizing this coding along with smart locks as previously mentioned, the system 130 either unlocks or prevents access. Selection of the worker's compensation activation element 238 may be required at the end of each workday or when an injury occurs. FIG. 2D provides a flowchart 260 of steps taken when the element 238 is activated 262. All workers may be required to enter this information each day. If the individual indicates that he/she has been injured 264, a video session with a claim agent is initiated 266. The claim agent may gather information to initiate any claim processing. The claim agent may determine if medical assistance is warranted 270. If medical help is warranted, the location of appropriate medical help is identified based on a location of the construction site (based on proximity and type of injury) and contact is made with the medical assistance (e.g., calling of an ambulance, hospital or urgent care facility) 272. The facilities may be chosen to be "in network" for the worker's compensation carrier. A confirmation of the claims may be generated 276 and sent to claims management 280. In addition, a report may be sent to the appropriate state authority 280. The steps 266, 270 and 272 may also be performed in the instance in which the individual has an older injury to report 268. Where there is no injury to the individual, the lack of injury is reported 274.

Delivery personnel may activate the delivery activatable element 226 (FIG. 2B). This causes a delivery functionality to be displayed where delivery notes may be added and where information may be gathered from the delivery person regarding a particular delivery. A contractor activatable element 228 may be selected by contractor individuals. Selection of this activatable element 228 causes the activation of the contractor functionality whereby the contractor may sign in, request tools, equipment, power or materials, leave notes or the like. Lastly, an inspector activatable element 230, may be activated to cause the inspector functionality to be activated. The inspector functionality may enable an inspector to add inspection notes, provide electronic inspection certificates and the like. The system can provide reports that can be automatically generated from the existing data described herein as well as notes manually added during the construction process. The reports can be generated at predetermined times such as daily or upon completion of specific tasks.

Figure 3A:
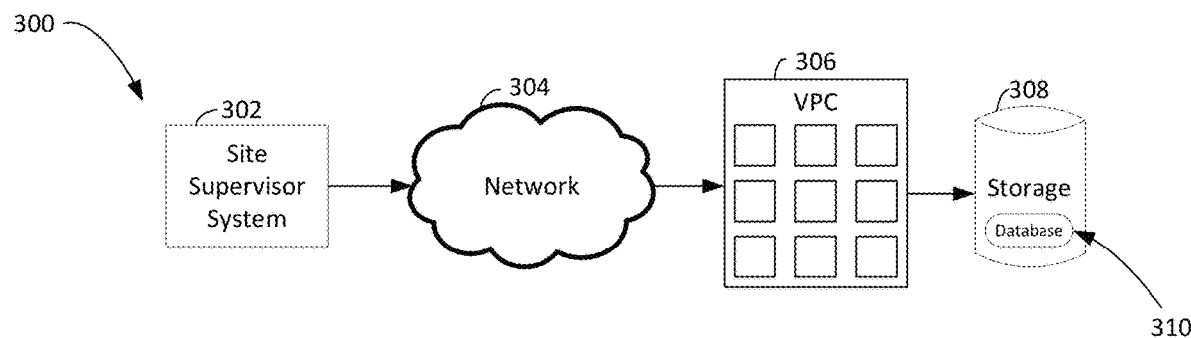
FIG. 3A shows an example of a communications environment.

As shown in FIG. 3A, the exemplary embodiments may be implemented in a decentralized computing environment 300, that may include distributed systems and cloud computing. FIG. 3A shows one or more systems 302 that may be in communication with a remote cluster 306 via a network 304. The cluster 306 may store information received from the system 302 and provide added computational functionality. The network may be a wired network or a wireless network or a combination thereof. The network 304 may be a secure internet connection extending between the system 302 and the cluster 306, such as a virtual private cloud (VPC). The server may be a computing device and can be in communications with the site computer device. The cluster 306 may include access to storage 308. The storage 308 may include a database 310 in which information regarding a construction site is stored in a consistent manner.

Figure 3B:
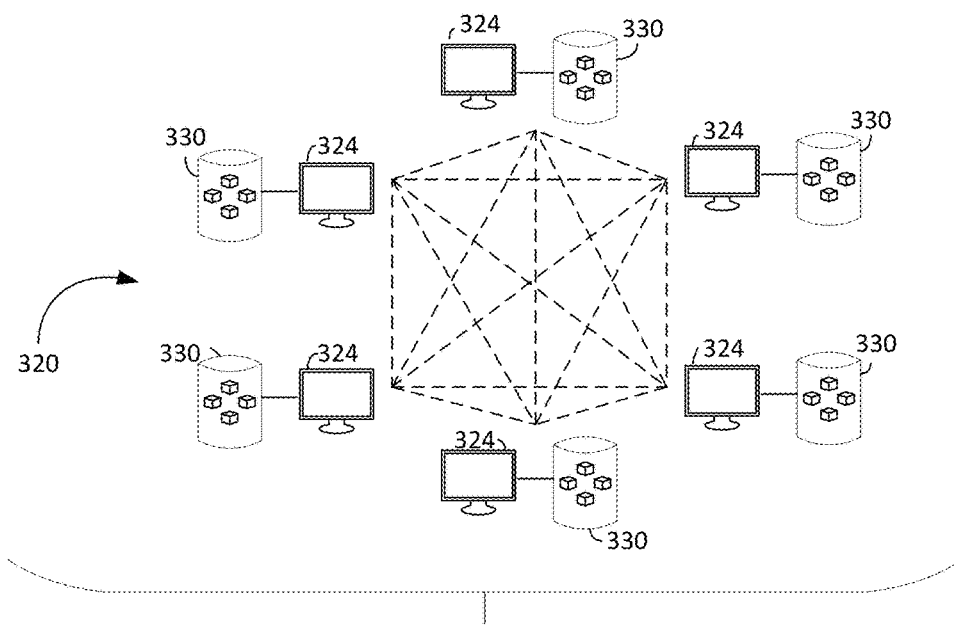
FIG. 3B shown an example of a distributed ledger.

FIG. 3B shows diagram 320 of an example of a peer-based network where a distributed ledger 330 is broadcast and shared among the nodes 324. This network may be resident in the VPC cluster 306 (FIG. 3A) or in the network 304 for example. The nodes 334 may represent computing resources, such as server computer systems or other computing systems, resident at the parties identified in FIG. 27, for example. Each node that has access to a copy of the persistent storage 330.

Figure 3C:
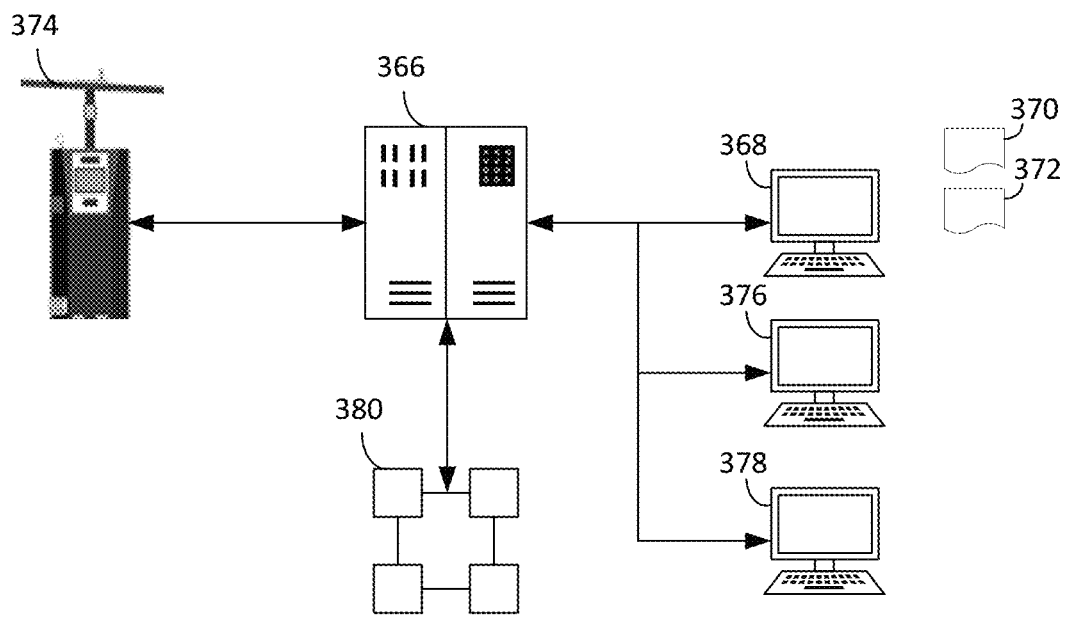
FIG. 3C shows a schematic of the aspects of the system.
Figure 3D:
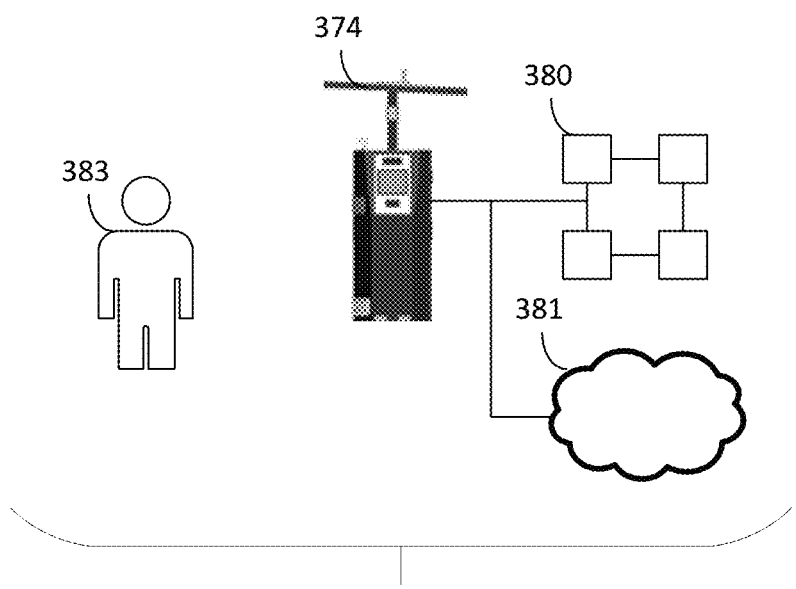
FIG. 3D shows a schematic of the aspects of the system.

Referring to FIG. 3C the server 366 can be in communications with design computing device 368 that can be used to transmit an architectural design 370 and bill of materials 372 to the server and kiosk or site computer device 374. The kiosk can be configured for receiving a planned bill of materials from a design company representing physical construction materials needed for the construction project, creating an actual bill of materials for the construction project representing the actual materials delivered to the construction site by a supply company, creating a final bill of materials according to a difference between the planned bill of materials and the actual bill of materials, receiving material installation information from the supply company representing the installation criteria for the actual materials delivered to the construction site, receiving installation verification information representing the actual material were installed by an authorized installer 383 (FIG. 3D) and under a set of compliant environmental conditions, receiving warranty criteria from the supply company representing the warranty requirements associated with the actual materials installed, determining if the warrant criteria are met, creating a certificate of warranty according to the final bill of materials and installation verification information, and storing the certificate of warranty on the distributed ledger.

Environmental conditions associated with an insurance event can include including physical location (e.g. GPS coordinates), weather conditions, impacted workers, impacted materials, impacted equipment, date and time, duration, pre and post events (e.g. chronologically relevant action(s), managers and supervisors on site and/or responsible. An insurance event can be an event, act or omission that affects the risk associated with insurance coverage. An insurance event can include an injury, loss, potential for an injury or loss, failure to supervise, misreporting or materials, workers, and the like that could cause an insurer to pay a claim or create the potential for an insurer to pay a claim.

Building material manufacturing specifications, which may be needed for compliance with warranty requirements, can be receive from a supply computer device 376 and regulatory code can be received from a regulatory computer device 378. The kiosk can include non-transitory computer readable instructions that when executed by a processor, provide the structure and function as described herein. Kiosk can receive a set of regulatory requirements associated with the construction site or project. The regulatory requirements can include approved construction materials that are approved by regulatory entities, such as governments, or designers, such as architects. Regulatory requirements can include building codes, fire codes, labor standards, building permit requirements, building and labor licenses, and the like. The regulatory requirements can include building and construction processes and procedures. For example, during construction, opening for windows and doors on second floors or higher should have safety railing installed. The type and quality of materials required for the construction project can be determined by the regulatory requirements. Compliance with the regulatory requirements can also be needed for a warranty to be honored. In some cases, when regulatory requirements are not followed, the warranty can be voided.

The various computer devices, including the server and site computer device (e.g. kiosk), can be in communications with persistent storage 380. The persistent storage can include a distributed ledger, immutable database, blockchain structure, and the like. The communications between the various computer device, including the server and the site computer device and immutable distributed ledger can be a global communications network, wide area network, local area network, deliver to a computer readable medium from one device to another (e.g. USB drive, CD, DVD) and can be wired or wireless.

The server can include a set of server computer readable instructions that can a set of server computer readable instructions stored on the server computer readable medium that, when executed by a processor included in the server, can be configured to: receive a building information model from a design computing device in communications with the server including an architectural design in compliance with regulatory code associated with a construction site and a bill of materials representing a set of materials to be used at the construction site according to the architectural design and a building material manufacturing specifications, store the building information model on the distributed ledger, transmit to the bill of material to a supply computer device informing a third-party supplier, distributor of reseller to deliver the materials to the construction site, receive a material delivery information representing that the set of materials to be used at the construction site has been physically delivered to the construction site, receive material installation information representing that the set of materials at the construction site has been installed at the construction site in compliance with a regulatory code and the building material manufacturing specifications, receive an internal inspection information from a site computer device in communications with the server representing that the installation of the set of material is in compliance with at least one of the architectural design, the bill of materials, the regulatory code and the manufacturing specifications, transmit an external inspection information request to an external inspection computer device in communications with the server; receive an external inspection information from a site computer device representing that the installation of a set of material as installed is in compliance with at least one of the architectural design, the bill of materials, the regulatory code and the manufacturing specifications, transmit the external inspection information confirmation to an external inspection computer device in communications with the server; debit a first account associated with the construction site and credit a second account associated with an external inspector, create a certification of code compliance according to the building information model, the material delivery information, the material delivery information, the internal inspection report and the external inspection report, and, store the certification of code compliance on the immutable distributed ledger.

The kiosk can be physically associated with the construction site and includes a computer readable medium and input interface. The construction site can be defined by a boundary representing the perimeter of the construction site. A set of computer readable instructions that, when executed by a site processor can be configured to: receive the bill of materials, receive the material delivery information, receive the material installation information, receive internal inspection information from a first inspector, receive external inspection information from a second inspector, and, transmit the material delivery information, the material installation information, the internal inspection information and the external inspection information to the server or to the persistent storage.

A set of computer readable instructions can be configured to store the bill of materials on the distributed ledger; and the supply computer device can be configured to retrieve the bill of materials from the distributed ledger or a designer, such as an architect. The kiosk can be in communications with the distributed ledger; and, the set of computer readable instructions can be configured to store the material delivery information, the material installation information, the internal inspection information and the external inspection information on the immutable distributed ledger. A reader can be in communications with the kiosk and configured to receive information from a tracking device; and, the set of computer readable instructions can be configured to receive material delivery information from the tracking device associated with the set of materials.

The reader can be selected from the group consisting of: radio frequency identification (RFID) detector, ultra-high frequency (UHF) detector, a bar code scanner, a QR code scanner, near frequency communication (NFC) device; an optical character recognition (OCR) device and any combination thereof. A environmental sensor, such as a weather sensor or weather station, can be in communications with the or included in the kiosk and configured to record the weather at the construction site, the computer readable instructions can be configured to capture installation weather conditions at the construction site at a time that the set of materials is installed and associate installation weather with the installation of the set of materials and transmit the installation weather to the server. The computer readable instructions of the server of kiosk can be configured to create the certification of warranty according to the installation weather following the manufacturing specifications for the installed material. The construction site can be associated with or identified by a physical location information such as global position (e.g. GPS) information. The kiosk can be on a movable platform including a cart, pallet, vehicle, trailer and the like.

Figure 4:
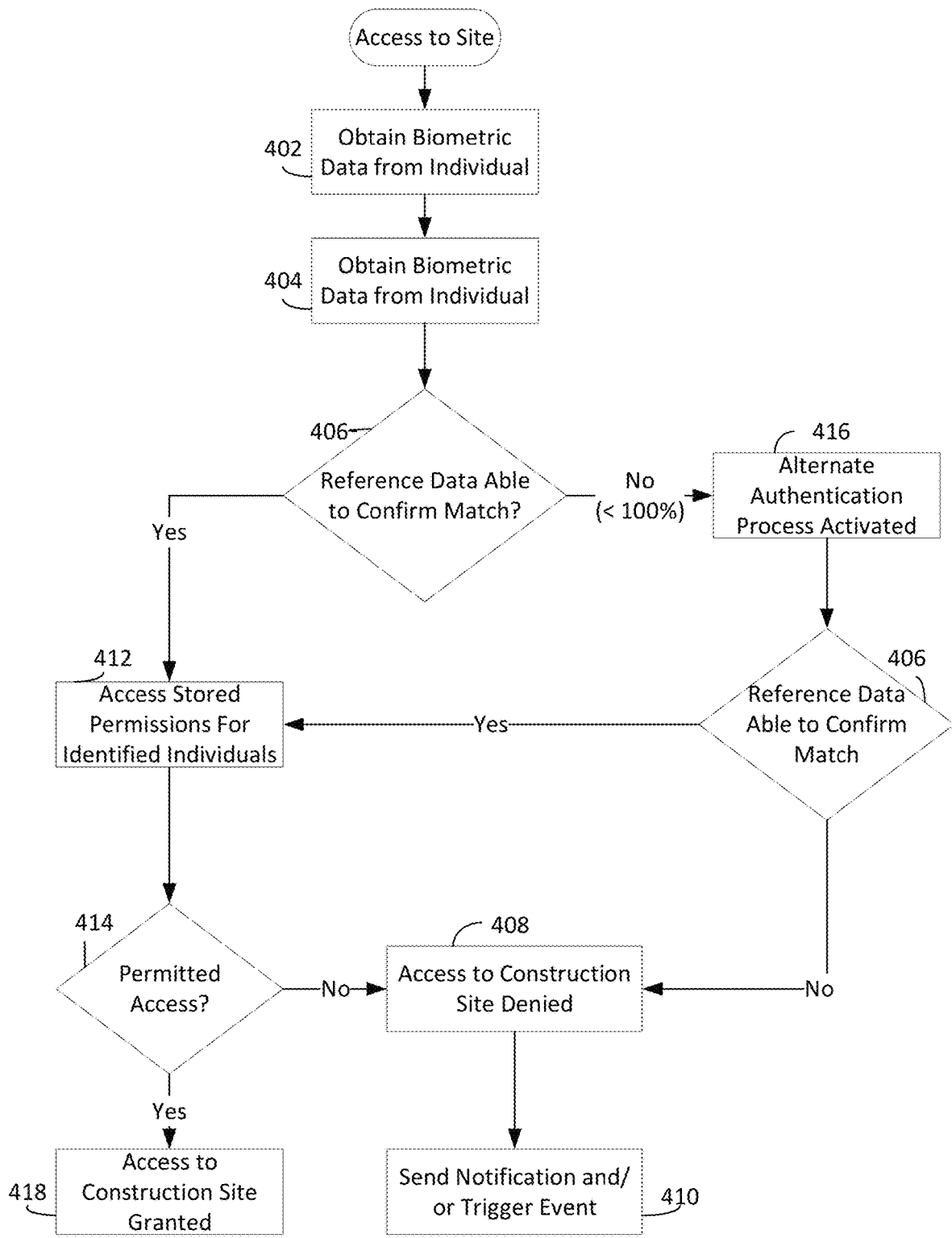
FIG. 4 shows a flowchart illustrating aspects of the system.

The system can control access to the construction site. FIG. 4 shows a flowchart 400 identifying steps that may be performed in exemplary embodiments regarding this functionality of the system. Initially, biometric data is obtained from an individual that is seeking access to the site 402. As was discussed relative to the example of FIG. 1A in some exemplary embodiments, a camera 102 may capture an image of an individual and facial recognition may be performed. The biometric data in this case is the facial image of the individual. In other exemplary embodiments, the biometric data may be, for example, fingerprint data, hand scan data, voice print data, retinal scan data or the like, gathered by appropriate biometric-based identification devices. The obtained biometric data is stored, and then previously stored data is accessed from storage to compare biometric data for known individuals and to attempt to identify the individual 404. A comparison may be made between the gathered biometric data and the known biometric data to determine if there is sufficient closeness for there to be a match. Information regarding the identity of the individuals for which the biometric data is stored is also stored in the storage device. A determination is then made whether there is a match or not 406.

If there is not a match 406, a manual process may be executed, or an alternative authentication process may be deployed 416. If this alternative authentication fails to produce a match 406, access to the construction site may be denied 408. In addition, a notification may be sent to a responsible party and/or an event may be triggered, such as contacting security or law enforcement officials 410. If the alternative authentication process produces a match, the process proceeds to 412.

The system may store permissions for each individual accessing the construction site. These permissions may identify the dates and times where the individual is given access to the construction site. In addition, the permissions may specify what tools, equipment or materials the individual is allowed to access. The permissions may specify whether the individual is allowed to use a power supply and may specify what portions of the construction site the individual is permitted to access. These permissions may be accessed to determine the permissions for the identified individual 412. If the permissions indicate that access is permitted 414, the individual may be granted access to the construction site 418.

Figure 5:
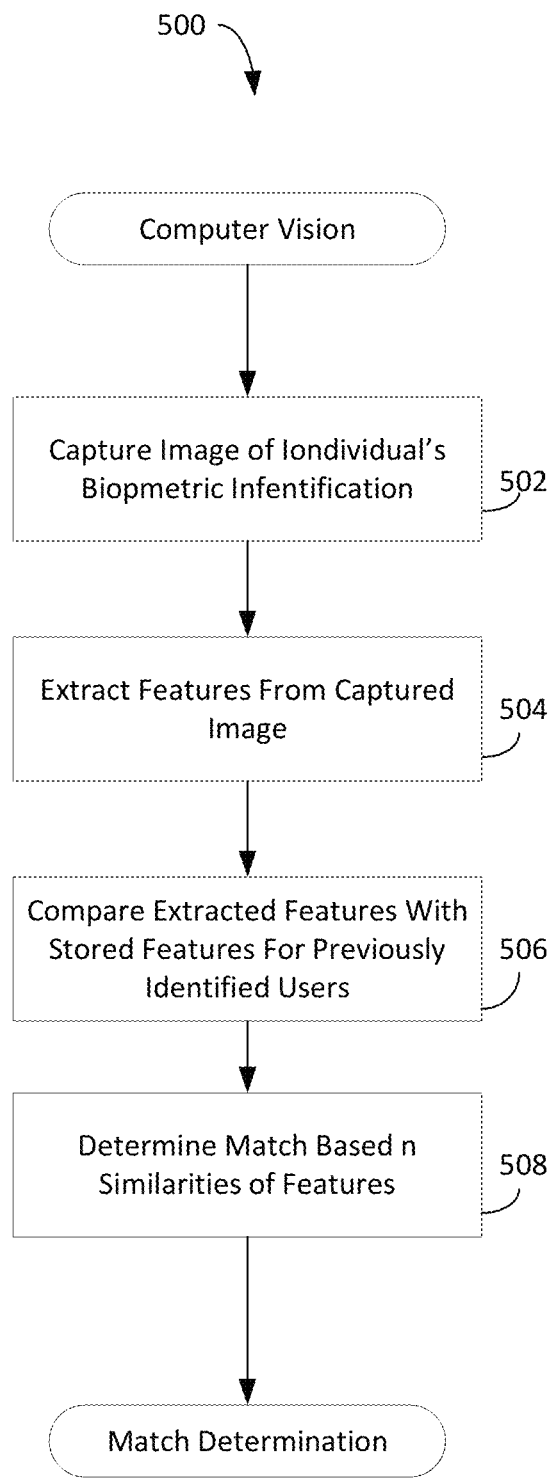
FIG. 5 shows a flowchart illustrating aspects of the system.

FIG. 5 shows steps that are performed in a case of computer vision for 402, 404 and 406 of FIG. 4. The flowchart 500, regarding computer vision, begins with 502 in which an image of an individual is captured for biometric recognition. This may be captured by a number of different types of image capture devices, including an intermittent video camera or other type of camera. In the case where an image of the face of an individual is captured, identifying features may be extracted from the captured image 504. In other words, unique facial features that help to identify an individual are extracted from the image. The image may be filtered and/or normalized. The features are then compared with the stored features for identified individuals 506, determination is made whether there is enough similarity for there to be a match.

FIG. 6 shows a diagram 600 that illustrates various types of biometric data 602 that may be obtained by biometric-based identification devices at the construction site to attempt to identify individuals. Biometric data may include facial recognition 603, an iris/retinal scan 604, a fingerprint scan 608, a hand scan 608, a voice print 610 or heart rate signature 614. It should be noted that other types 612 of biometric data may also be used in exemplary embodiments to help identify individuals uniquely. Also, an individual may be required to provide multiple types of biometric data in some instances.

As was mentioned above, when individuals attempt to access the construction site and is not granted access, certain events may be triggered (see 410 in FIG. 4). FIG. 7 shows a diagram 700 that provides an example of different types of triggered events 702. One type of triggered event is an alarm 704. This alarm may include visual alerts, audio alerts or a combination thereof. The alarm may be a silent alarm to individuals. Another event that may be triggered is to send notifications to a supervisor for the construction site 706. The supervisor may, for example, receive an email, a text, phone call or other notification that someone is trying to access the site that is not permitted. A triggered event 702 may also include the contacting of law enforcement or a member of a security service indicating that an unauthorized party has tried to access the construction site. Lastly, a triggered event 702 may include prompting the individual to produce proper identifying information to an official at the site or to a scanning device at the kiosk 100.

One type of individual is a contractor. FIG. 8 shows a flowchart of the steps that may be performed to ensure that the contractors gain access to the appropriate items once they have been granted access to the construction site. As shown in the flowchart 800 of FIG. 8, initially the contractor has their identity confirmed, as has been discussed above 802. The system may offer an alternative touchscreen option to place a call to the appropriate party should the software fail to verify an otherwise authorized individual. The contractor may be prompted to interact with the display, such as the touchscreen 106B (FIG. 1) to register and to indicate whether they seek certain items. For example, with the user interface of FIG. 2B, the contractor may activate the contractor activatable element 228. Access is then granted to wearables and/or tools and/or equipment 806. The wearables, the tools and/or equipment may be stored in sheds or in other secured locations under the control of smart locks that may be controlled by the computing system of the system.

FIG. 9 provides a flowchart 900 of the steps that may be performed relative to smart locks at the construction site. The individual, such as a contractor, has his/her identity determined and has access to the construction site 902. The system may offer an alternative touchscreen option to place a call to the appropriate party should the software fail to verify an otherwise authorized individual. The permissions stored for the individual are accessed 904. A determination is made whether the individual is granted access to a smart locked area 906. If the individual has permission to access the area 908, the smart locks may be activated to unlock the area, such as where wearables, tools or equipment are located. Before the individual can use the tools/equipment, the individual may first be required to wear some of the wearables and to scan the tools or equipment to indicate that they will be using the tools or equipment. If the individual lacks the proper permissions to access the area, then access to the area is denied 910, such as by keeping the smart locks locked. In one embodiment, the tools and equipment used can be determined so that the proper tools are used for installation of materials if required for warranty requirement compliance.

Figures 10, 11:
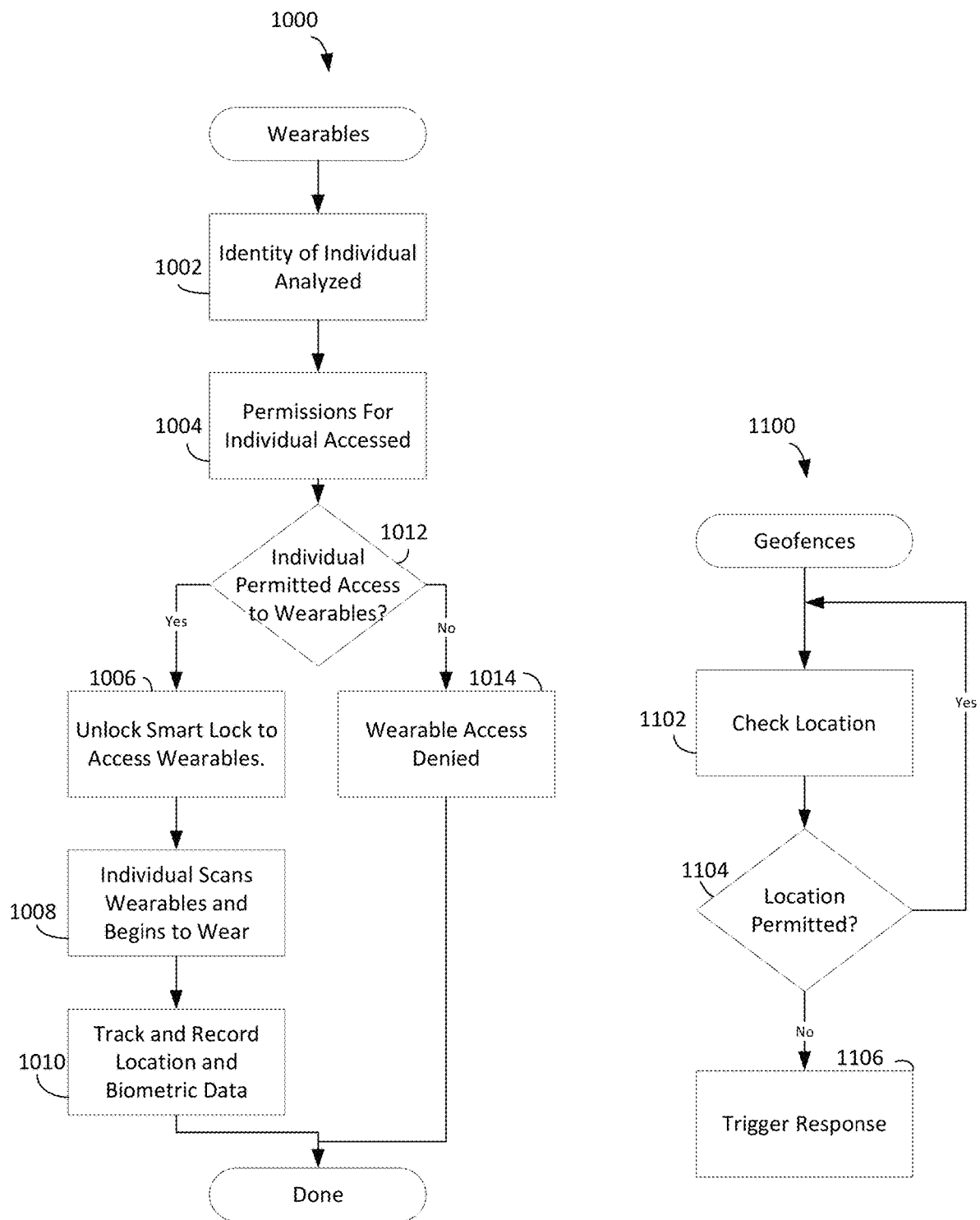
FIG. 10 shows a flowchart illustrating aspects of the system.
FIG. 11 shows a flowchart illustrating aspects of the system.

FIG. 10 contains a flowchart 1000 illustrating the steps that may be performed to obtain the wearables. For some individuals, a wearable can be provided to the individual prior to interaction with the system and used to register with the system. This individual can receive the wearable and upon approaching a kiosk, be registered with the system when the individual reaches a certain proximity to the system.

The wearables may include safety gear, such as hard hats, gloves, goggles, vests and the like, as well as wearables for tracking and obtaining biometric data. The identity of the individual is confirmed 1002, and the permissions for the individual are accessed 1004 and a determination is made based on the permissions if the individual should be granted access to the wearables 1012. The system may offer an alternative touchscreen option to place a call to the appropriate party should the software fail to verify an otherwise authorized individual. If it is determined that the individual should be granted access, the smart lock for the storage location of the wearables is unlocked 1006. The individual may then be prompted to scan information regarding the wearables so as to register the wearables and associate the wearables with the individual 1008. In one embodiment, the system may use one or more images of an individual to determine if the individual has the necessary safety equipment. For example, an image of the individual taken by the kiosk can be used to determine if the individual is wearing a hardhat and generate a warning if no hardhat is present.

The system may require that an individual wear certain safety equipment in the form of wearables. The system may record what wearable the individual scans. The system tracks and records the location and biometric data gathered by the wearables 1010. The wearables may include smart vests, bracelets, badges, sensors and the like that provide location information and biometric data, such as heart rate, body temperature, blood pressure breathing rate, gyroscopic informatic and/or other information. These wearables assist the system in tracking the location of individuals of the construction site. These wearables also help to track the biometric data of individuals. The biometric data may be helpful in identifying that an individual is experiencing an accident, a health event or is idle. The biometric data is stored so that a record of the biometric data can be kept. If in 1005, it is determined based on the permissions that the individual should not be granted access, then access to the wearables is denied 1014.

The use of the wearable to track location helps to facilitate use and installation of material to determine warranty requirement compliance. The wearable information can be combined with geofencing in an exemplary embodiment. The geofencing enables the system to track and limit access to locations of individuals at the construction site. The construction site may be partitioned into areas where different permission rights are given for the various areas. For example, a plumber may be given access to the kitchen and the bathrooms of a project under construction but may be prohibited from being in the living room or the roof. As shown in FIG. 11, a flowchart 1100 shows some of the steps performed automatically and can be performed without notification to an individual. The process begins with the checking of the location 1102 of an individual. A determination is made in 1104 whether the individual is permitted to be at that location. If the individual is not permitted to be at that location, a response is triggered 1106.

Figure 12A:
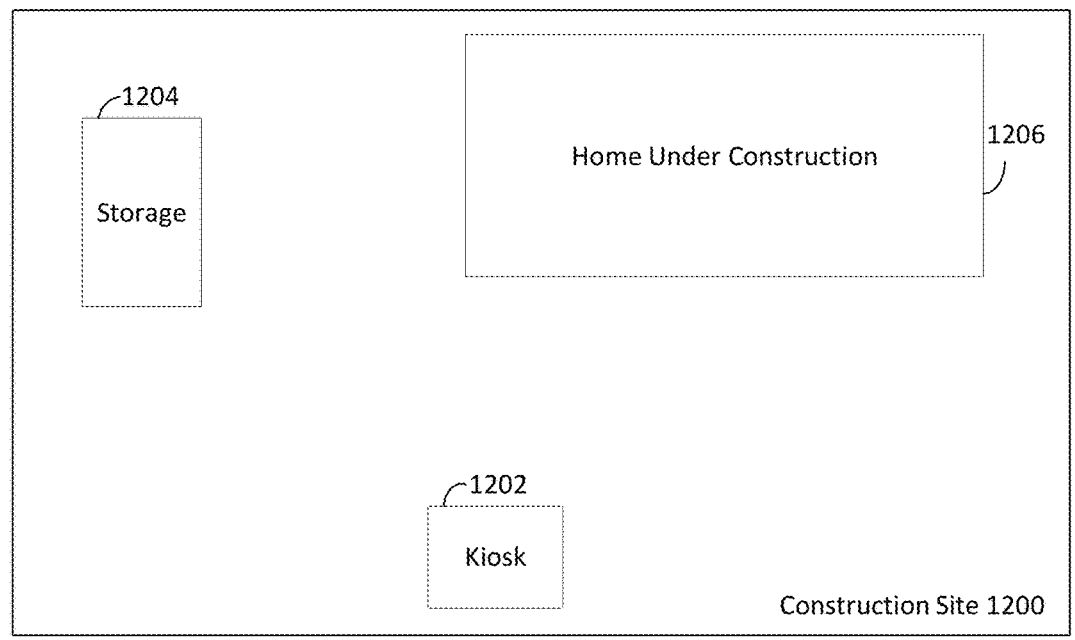
FIG. 12A shows a plan view of a construction site.

To help illustrate an example of geofencing, FIG. 12A shows an illustrative construction site 1200. The construction site 1200 may include a kiosk 1202 for the system as well as storage location 1204 that can be a building, trailer, shed or the like. The storage location 1204 may hold tools, equipment, wearables and/or materials. The construction site 1200 may also include a home or other building project that is under construction 1206.

Figure 12B:
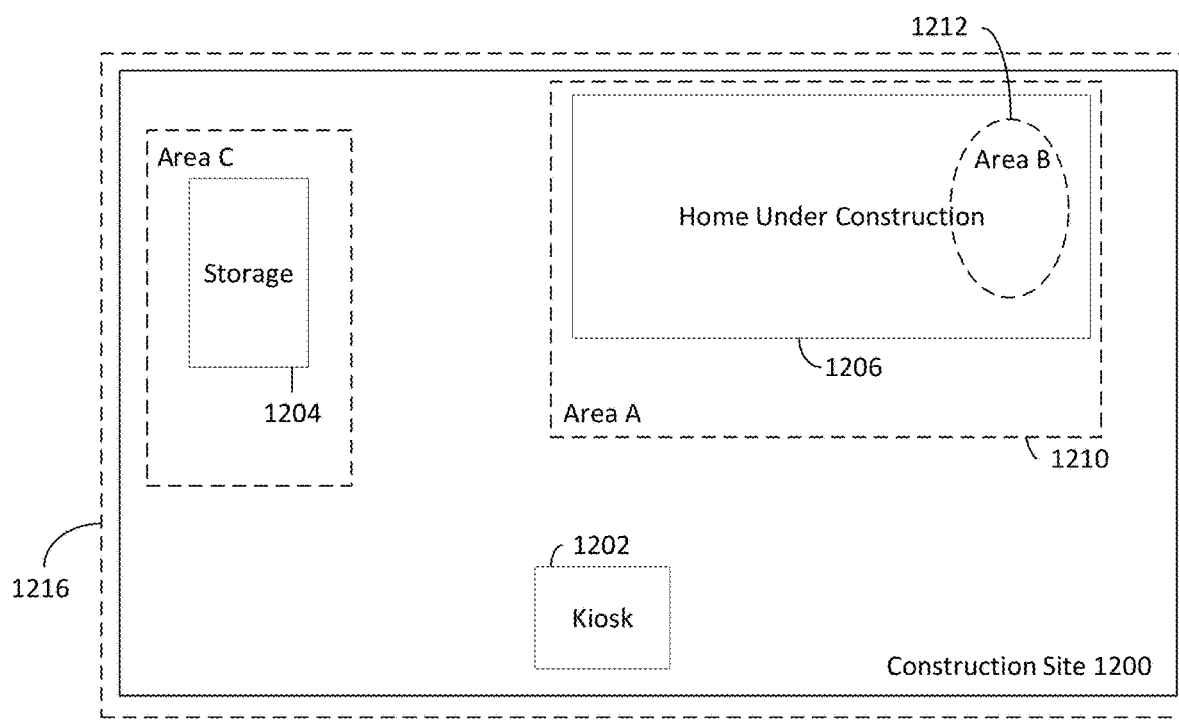
FIG. 12B shows geofencing areas at a construction site.
Figure 13:
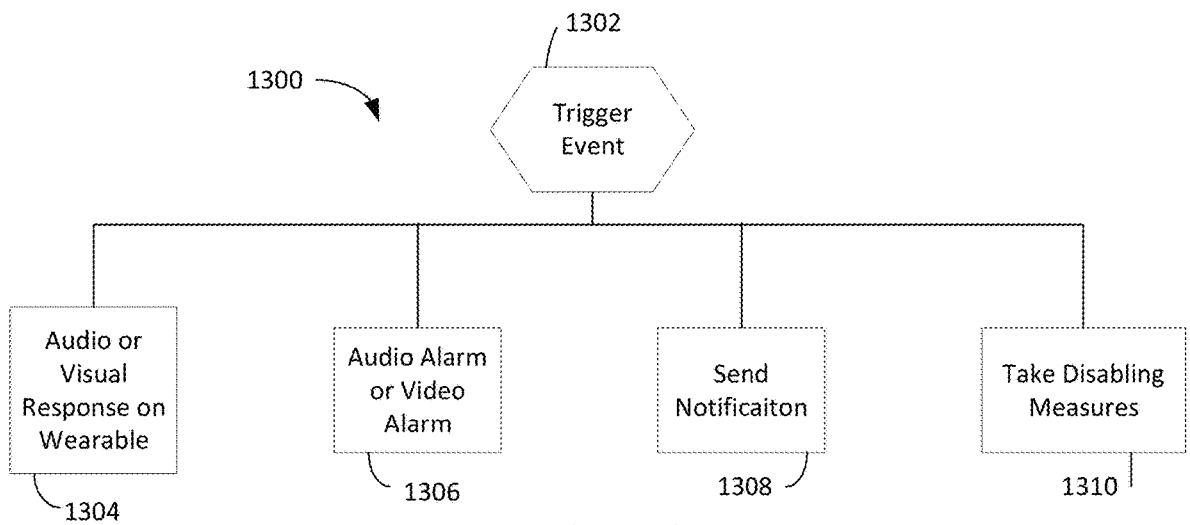
FIGS. 13-16B shows flowchart having steps that may be performed.
Figure 14:
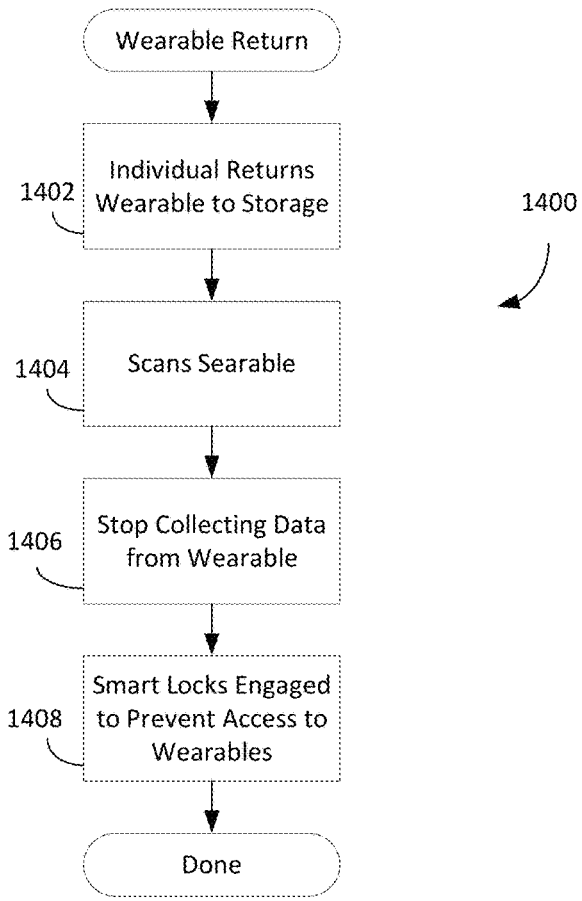
Figure 15:
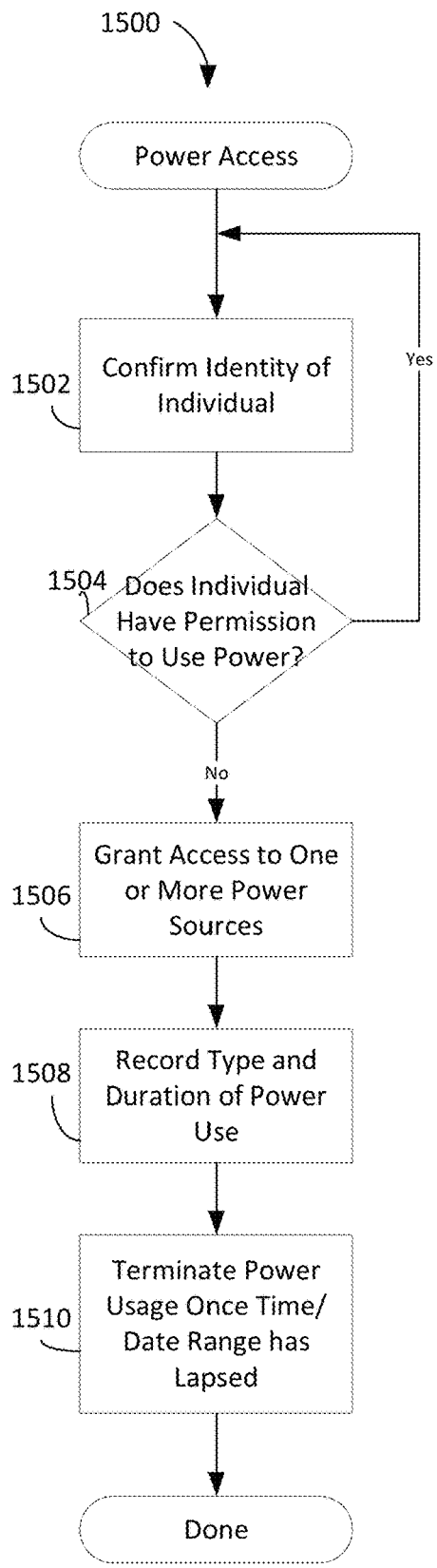
Figure 16A:
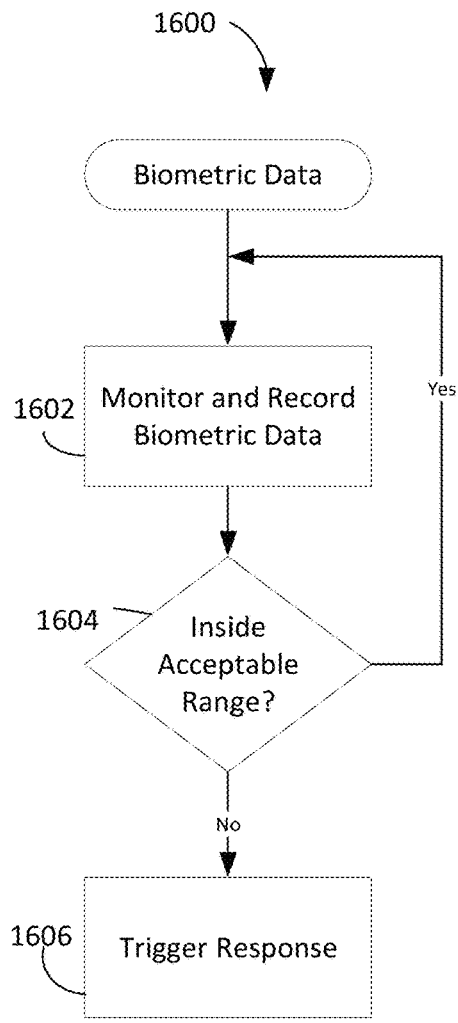
Figure 16B:
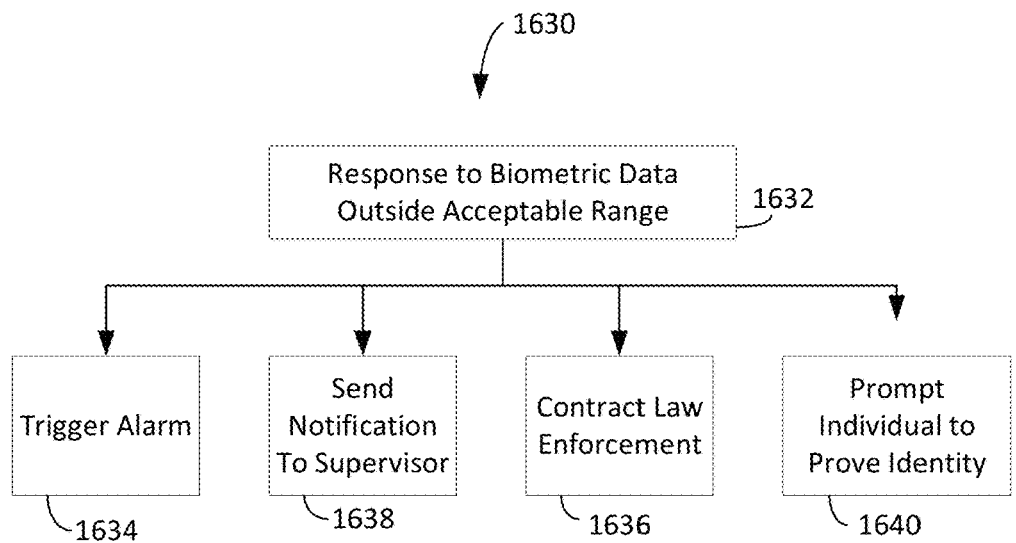

FIG. 12B shows an example of different areas that may be established for geofencing at the construction site 1200. Area A shown a boundary 1210 may include the entirety of the project that is under construction 1206. Area B 1212 may be a portion of the project, such as the kitchen. Area C 1214 may be the shed and area D 1216 may be the entire construction site. Individuals may have access to none of these areas or to a subset of these areas, including all of the areas.

When a worker enters an unauthorized area, an audio or video response can occur on the wearable. For example, a smart vest may include lights that may flash or may be continuously illuminated in response to a party being outside the permitted areas on the construction site. Another option is for an audio alarm or a video alarm to be triggered at the construction site rather than on a wearable. A further option is to send a notification, such as a phone call, a text message, an email message or other notification to a supervisor on or off the construction site. Yet another option is to take disabling measures relative to the individual. The disabling measures could entail triggering locks or disabling equipment by shutting off power or the like. The geofencing can also be used to determine where material delivered, stored, and installed. The geofencing, along with date and time information, can assist with the determination whether the material was handled or installed by a licensed, experience, approved, authorized or otherwise preferred worker.

Figure 17:
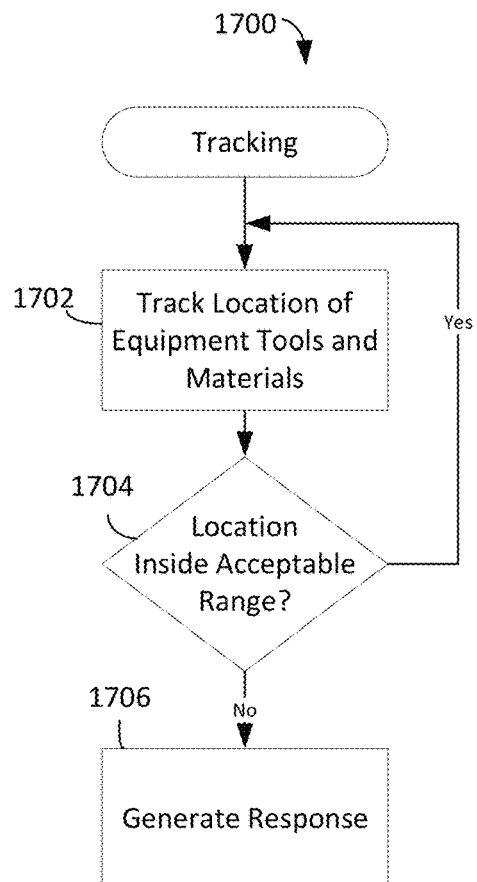
FIG. 17 shows a flowchart illustrating steps that may be performed.

FIG. 17 shows a flowchart of steps that may be performed relative to such tracking. On an ongoing basis, the system may track the location of equipment, tools or materials at the construction site 1702. The system can check whether the location of the equipment, tools or materials is acceptable or not 1704. For example, suppose that lumber has been delivered to the construction site and the location of the lumber indicates that the lumber is removed from the construction site. This would be problematic and would warrant a response. If the location is not acceptable as checked in 1704, a response is generated in 1706.

Figure 18:
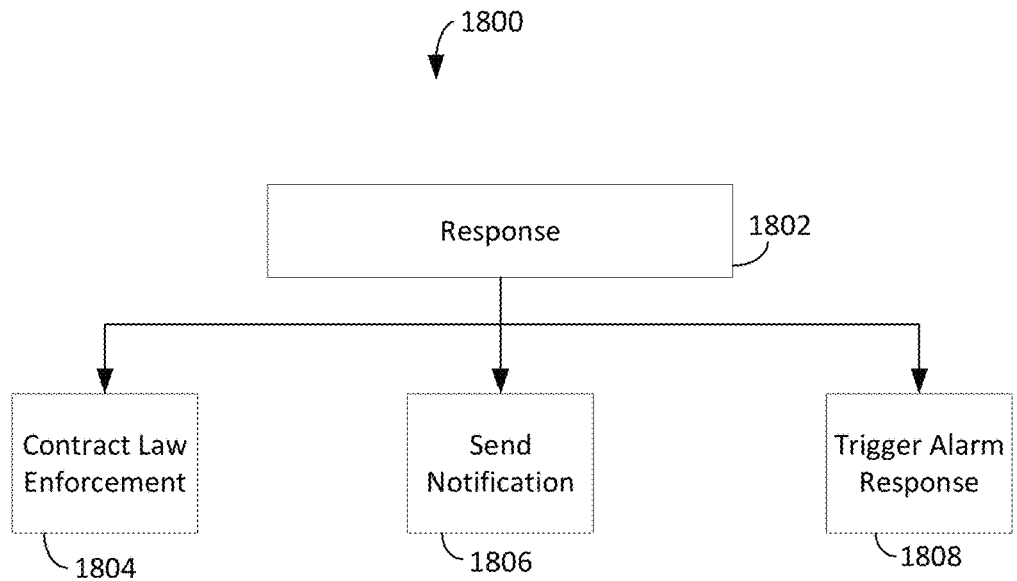
FIG. 18 shows possible responses accomplished by the system.

FIG. 18 shows a diagram 1800 illustrating different types of responses 1802 that may be generated in response to the equipment, tools or material in an unacceptable location. One type of response is to contact law enforcement or security 1804. In many cases the location of the tools, equipment and materials may indicate that a theft is underway. Another type of response is to send a notification to supervisor or to other appropriate parties at the construction site 1806. A final type of response is to trigger an alarm response 1808, such as the sounding of an audio alarm or a video alarm.

Figure 19:
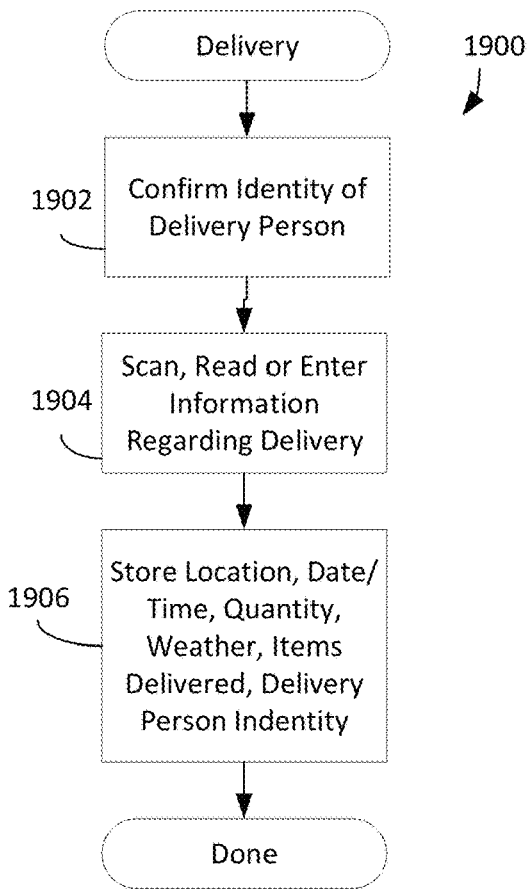
FIG. 19 shows a flowchart illustrating steps that may be performed.

The system helps manage deliveries to the site. FIG. 19 depicts a flowchart 1900 showing steps that may be performed in this regard regarding deliveries. Initially, the identity of the delivery person is confirmed to indicate that the delivery person is the appropriate party and is permitted access to the construction site 1902. For example, a serial number or other identification indicator may be scanned or read off the delivered items. In addition, information may be entered by the delivery person using the kiosk, such as by entering information via screen 106A (FIG. 1A) 1904. The location of delivery, the date of delivery, the time of the delivery, the quantity of delivery, the identity of the delivery person and the weather may be recorded as part of the information that is kept regarding the delivery. This information can be used to track and confirm deliveries as well as to understand the conditions when the delivery was made.

Figure 20:
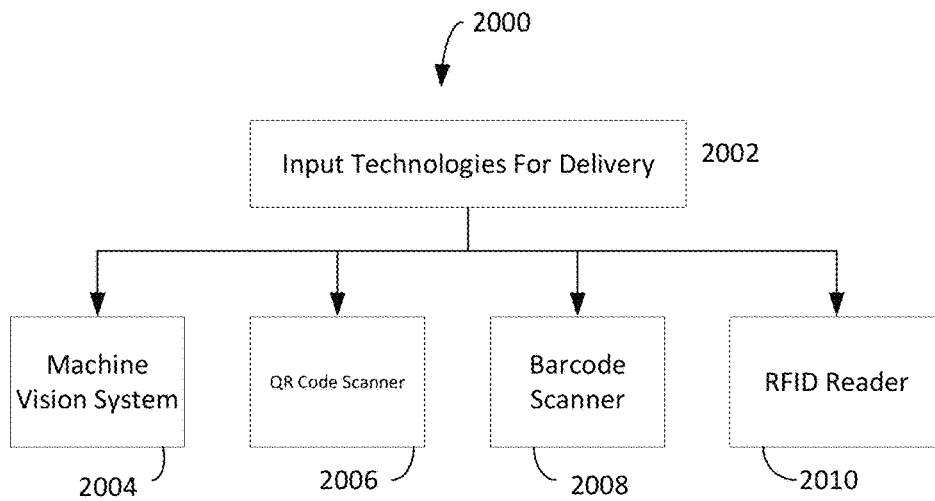
FIG. 20 shows different types of input technology.

The deliveries may utilize various scanning and reader technology. In FIG. 1A, a scanner 110A may be provided. Diagram 2000 in FIG. 20 illustrates different types of input technologies 2002 that may be used for assisting gathering information regarding deliveries. A machine vision system 2004 may be provided. The machine vision system 2004 may capture an image of the delivered items and process the image to determine the nature of the items that were delivered as well as the quantity of items. Moreover, the machine vision system may capture an archival image that may be indicative of the state of the items when they were delivered. A QR code scanner 2006 may be used where QR codes are on a delivered items or documentation. Similarly, a bar code scanner 2008 may be used where bar codes are on the items or on documentation delivered with the items. Still further, an RFID reader 2010 may be provided to gather information regarding the delivered items.

Figure 21:
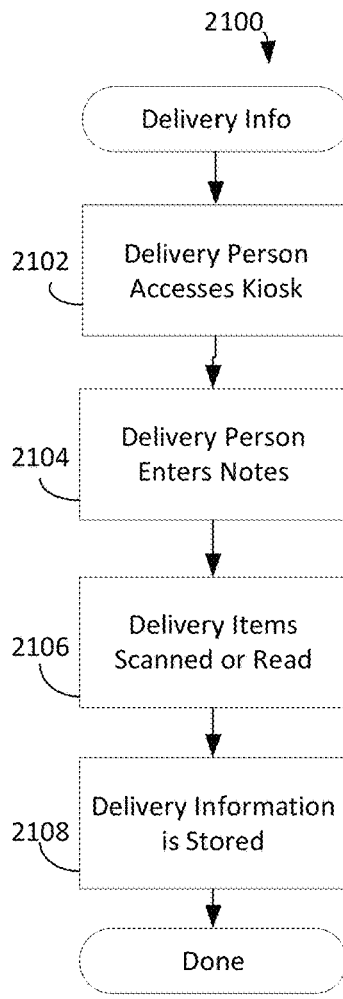
FIGS. 21-27 shows flowcharts steps that may be performed.

The delivery person may interface with kiosk via display 106A and 1900 to provide delivery information. Flowchart 2100 of FIG. 21 illustrates some of the steps that may be performed in such an instance. Initially, the delivery person may access the kiosk 2102. The delivery person may enter a note(s) regarding the delivery, such as what was delivered and the state of items that were delivered 2104. This information may be entered, such as through the display 106A (FIG. 1A) which can be a touchscreen. The delivered items are imaged, scanned or read 2106. As was mentioned above, a number of different types of input technology may be used on the delivered items. Therefore, delivery information is then stored in records that may be accessed subsequently 2108.

Figures 22, 23:
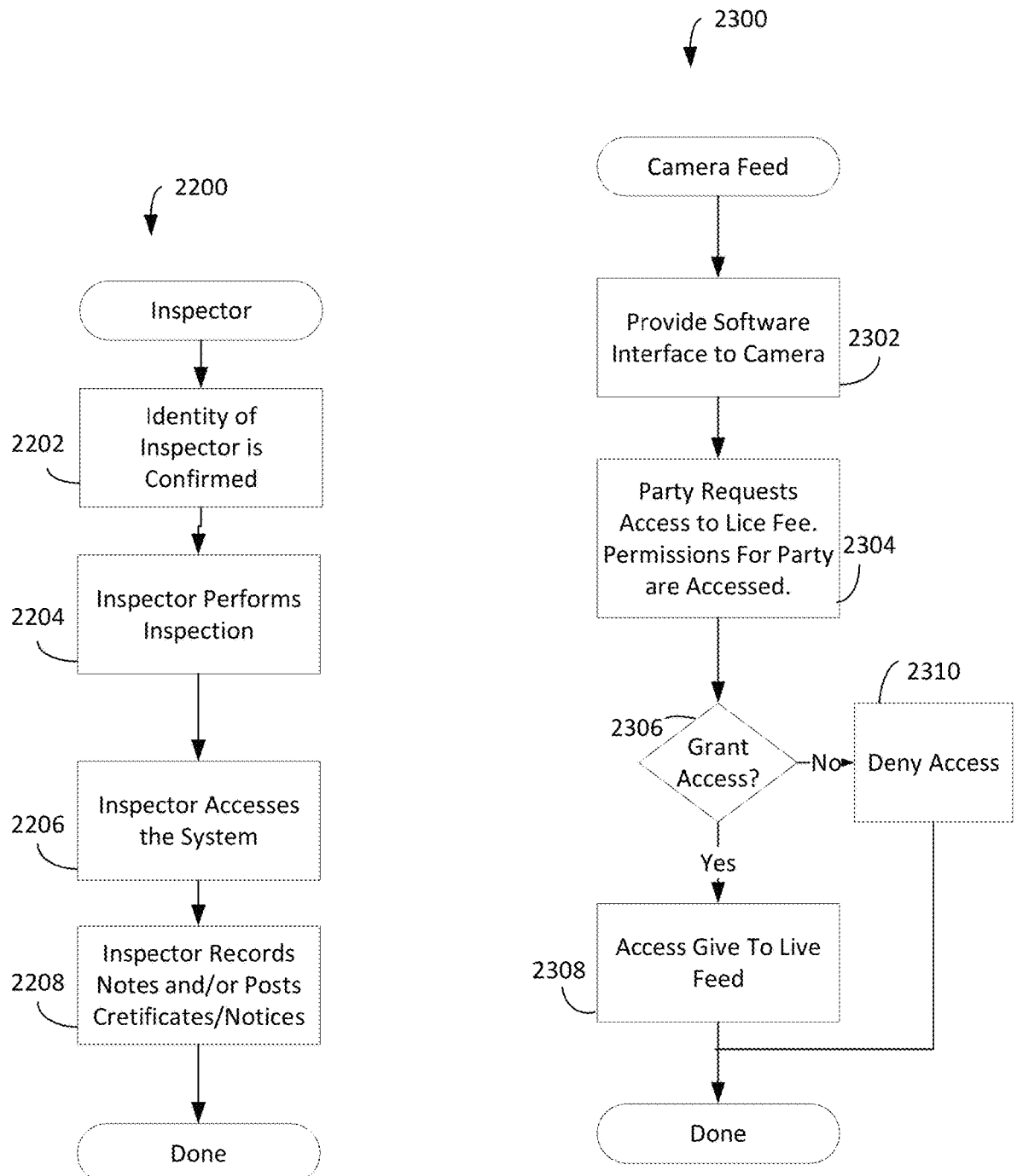

The inspector may interface with the system. FIG. 22 includes a flowchart 2200 illustrating steps that may be performed in such an interaction. Initially, the identity of the inspector may be confirmed using the biometric data 2202 or manually using the touchscreen on the kiosk. The inspector then performs the inspection of the appropriate portion of the construction site 2204. The inspector then accesses the system, such as through the kiosk at 2006. The inspector then may record notes and/or post certificates or notices at the kiosk 2208. Additionally, the inspector may use technology available via the kiosk such as OCR scanner or the like to capture appropriate information the inspector may have written during fulfillment of the reason for being on the site.

The system may include a still camera(s) or a video camera(s) that can be included in the kiosk. FIG. 23 provides a flowchart 2300 relating to such access. A software interface to the camera may be provided to enable authorized external parties to gain access to the camera 2302. A party requests access to the camera via the interface over the network 2304. For example, a bank official may wish to view the construction site before authorizing release of funds or before granting a loan. A determination is made whether the party is permitted access by accessing permissions 2306. The system gathers a great deal of information over the course of time. At least a portion of this information is persistently stored to compile a record of activities at the construction site. This record can be useful to prove activities after the fact. The activities that are recorded may drive workflow and scheduling at the construction site to improve efficiency. If the party is permitted access, access is given to the party so that they may receive a captured image or video data 2308. Otherwise, access to the camera by the party is denied 2310.

Figures 24, 25:
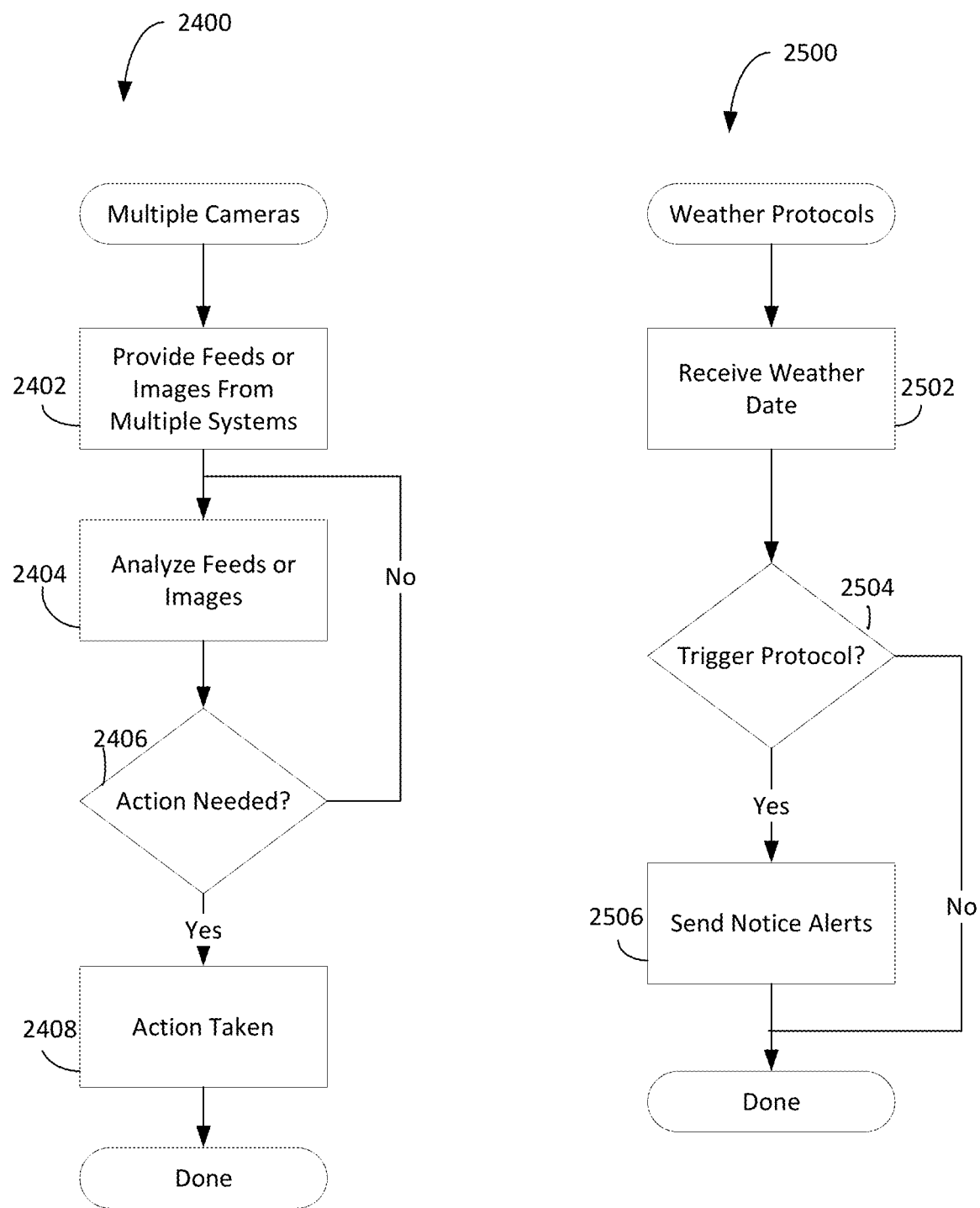

Systems at adjacent locations may be used in conjunction with each other. FIG. 24 shows a flowchart 2400 of steps that may be performed when image capture devices, such as still cameras or video cameras, from multiple adjacently situated systems are used in conjunction in one example application. Video feeds or still images may be obtained from the image capture devices from multiple systems 2402. The video feeds or images may then be processed, such as by the cluster described above, using software such as motion detection software, thermal image analysis or other image analysis software to identify activity that may warrant a response 2404. For example, the analysis may identify a large living object moving near the periphery of multiple construction sites. The system may then, based on the analysis, determine if action needs to be taken 2406. If an action is needed, then the action is taken 2408. If not, the capture of the images or videos may continue. Examples of actions include sounding an alarm, contacting law enforcement, contacting a security team or the like.

The weather conditions may trigger different protocols that are performed by the system. For example, inclement weather, very cold weather or very hot weather may trigger protocols to ensure worker safety and productivity as well as the protection of structures, materials, and equipment at the construction site. FIG. 25 shows a flowchart 2500 of steps that relate to such protocols. Initially, the system receives weather data 2502. A check is made whether the weather data values trigger any protocols 2504. If a protocol is triggered, notices and alerts may be sent as part of the protocol to the appropriate parties 2506. For example, if the temperature is over 90° F., a party may be sent a notice to take a break every hour and to hydrate. Related notices may be sent to supervisors. Such notices can be generated according to the product or material specifications in the BOM, when materials are confirming or nonconforming, environmental conditions and other events. For example, if it is too cold, workers may be prompted to wear gloves and hats and to spend time in a heated space every hour. In still another example, if severe weather is approaching, workers may be prompted to secure the construction site and seek a safe location. In a final example, workers may be prompted not to take actions, such as pouring concrete, applying paint, or applying stucco, in certain weather conditions.

Figure 26:
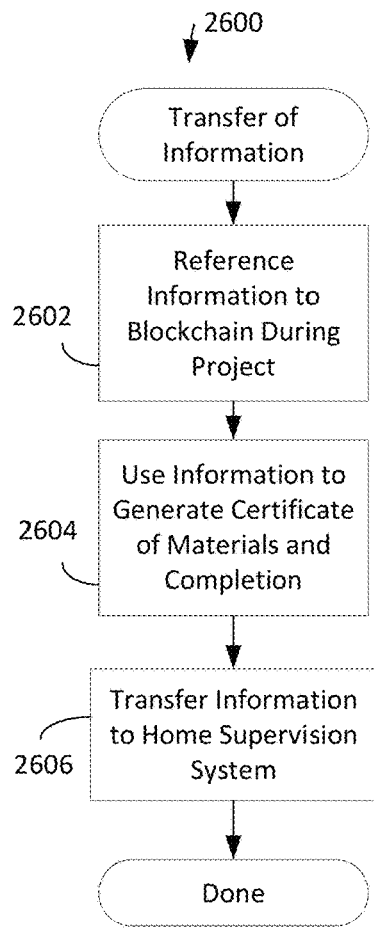

As has been mentioned above, a great deal of information may be stored during the construction project for reference during the project and after the project is completed. FIG. 26 shows a flowchart of steps 2600 that may be performed in exemplary embodiments in relation to the information. The information obtained during the project from many different sources may be stored on or referenced from persistent storage 2602. The information may be stored on an ongoing fashion in databases as describe below and may be referenced in an immutable persistent fashion on the immutable distributed ledger. This information may help resolve disputes between parties involved on the construction project. For example, suppose the construction company asserts that the wrong items were delivered. Since there is a complete record references on the persistent storage of all deliveries, these records may be accessed to resolve the dispute. Insurance providers may access injury records referenced on the persistent storage to settle or confirm claims. Disputes regarding pay among workers may be resolved by checking the recorded hours on site to determine the appropriate pay for the workers. Inspection records may be accessed to confirm that proper inspections were carried out and passed.

When the construction project is complete, information referenced on the persistent storage may be extracted and encapsulated into a certification of materials and completion 2604. The certificate of completion can be created based upon the kiosk receiving a set of completion criteria from the regulatory entity and a financial entity, determining whether the set of compliance criteria has been met according to the certificate of regulatory compliance, the certificate of materials the certificate of inspection, a payment information representing that payments have been satisfied, and occupancy requirements have been met. The certificate of completion can be stored on the persistent storage.

The certificate may hold information such as the BIM, the final BOM, worker sequence information, warranties for items in the completed home, confirmation of conditions and qualifications at the time of installation for warranty, punch list completion information, lender information, information regarding the contractors and workers, insurance policy information, inspection history information, ownership history, history of localized events like weather and records of trespassing (such as images) and bills of lading for items delivered during the project. The certificate may be delivered in electronic form and preferably in an immutable format. Alternatively, the certificate may be delivered in paper form. The certificate may be delivered to the owner of the property or to a property manager. In addition, the certificate may be passed to other interested parties, such as an insurance provider or financial institution.

A few examples help to illustrate the value of the certificate. The certificate acts as a complete record of the project. Suppose that an oven in a home fails 3 months after an owner occupies the premises. Since the certificate has complete warranty information, the owner can reference the warranty information and get the oven fixed under warranty. As another example, suppose that gutters on the home leak 6 months after an owner occupies the premises. The owner can reference the certificate to contact the contractor, construction company or manufacturer. The construction company might also have a remedy against the installation contractor based on evidence that materials were not installed properly or the manufacturer if the condition precedent were not confirmed or not met. Further, the bills of lading (BOLs) may indicate that the materials delivered were different from those specified in the BIM and BOM. The certificate may also assist in obtaining a lower insurance premium from a provider because be reducing or eliminating unknowns about the project.

The information referenced in the persistent storage may also be passed to a computing device of the owner 2606. The computing device may be, for example, part of a home supervisor system that manages and controls home systems, such as heating, air conditioning, lighting, an alarm system, or the like. The computing device may be part of a smart home controller and may interface with appliances and other items that are interconnected via a home control network.

The computing device may include a document management system for securely storing the transferred information.

In exemplary embodiments, information may be gathered from and sent to multiple parties including a managing company responsible for the management and oversight of the construction project, a design company responsible for developing a design for the home and develops the BIM for the project, a supply company analyzes the BIM and develops a BOM for the construction project, and a construction company is responsible for constructing and assembling the home.

Figure 28A:
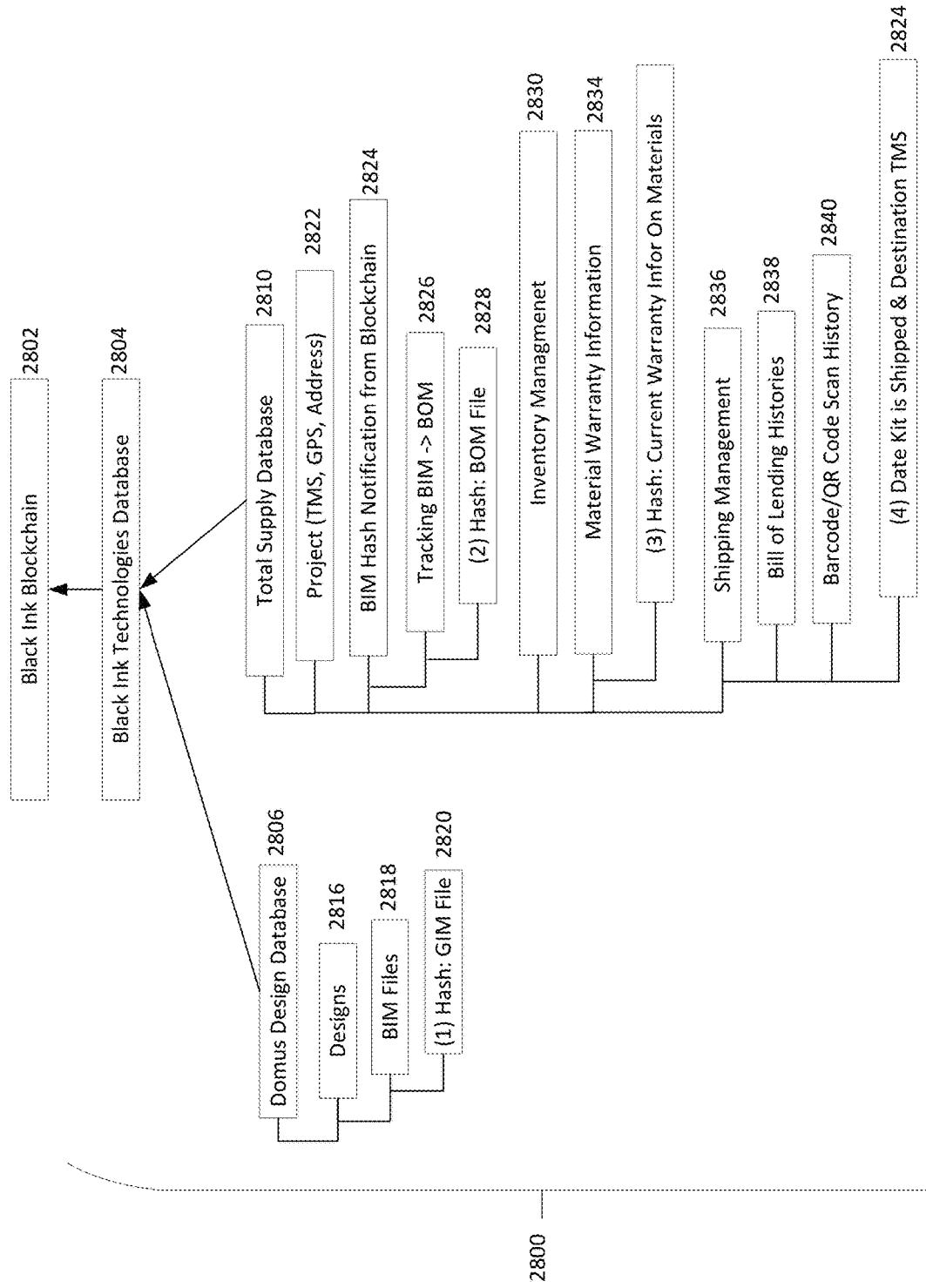
FIGS. 28A-29 shows databases that provide reference information.
Figure 28B:
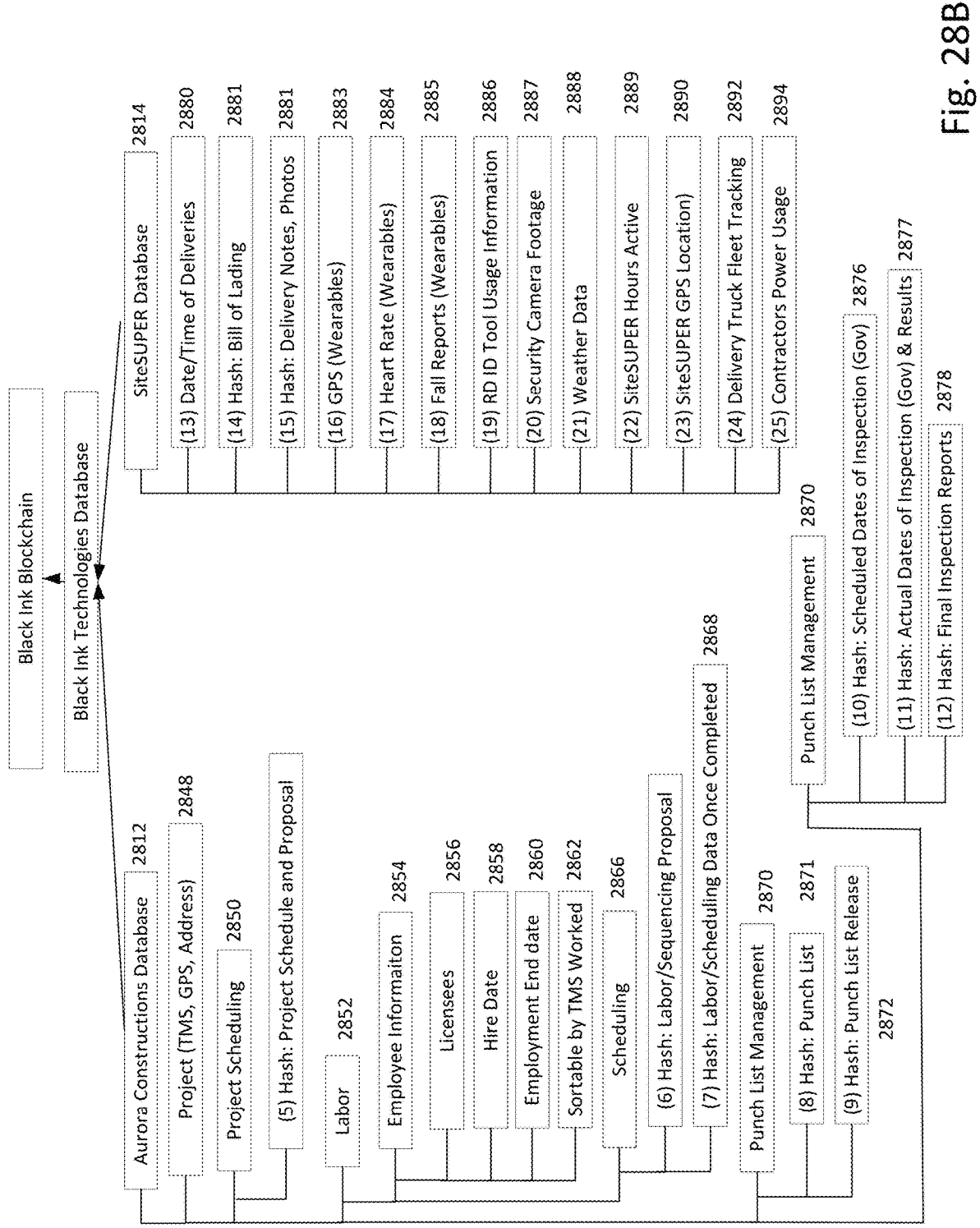

FIGS. 28A and 28B show a diagram 2800 depicting possible information from multiple data sources (e.g., databases), some of which may be referenced on the persistent storage 2802. The workflow may be that the data is first stored in a management company database 2804 and then referenced on the persistent storage 2802. The design company database 2806 may hold information that is passed on to the management company database 2804 and ultimately referenced on the persistent storage 2802. The design company database 2806 may hold designs 2816. The designs 2816 may include BIM files for BIMs, as has been discussed above. A hash value resulting from passing the BIM file 2820 for the construction project through a secure hash algorithm may also be stored on the design company database 2806. The BIM file may be hashed using any number of different types of known secure hash algorithms as mentioned above. The hash value of the BIM file may be transferred to the management company database 2804 and then for reference on the persistent storage 2802.

FIGS. 28A and 28B show a supply company database 2810. The supply company database 2810 may hold project information 2822, such as tax map submap (TMS) numbers, GPS data and addresses for construction project properties. The supply company database 2810 may store a BIM hash notification 2824 from the persistent storage 2802, indicating that the hash value for the BIM has been referenced on the persistent storage 2802. Information 2826 tracking the bill of materials (BOM) to the BIM may be stored in the supply company database. As was discussed above, the supply company may analyze and process the BIM to develop of BOM for the project. A hash value 2828 resulting from passing the BOM file through a secure hash function is stored in the supply company database 2810, transferred to the management company database 2804 and referenced on the persistent storage 2802.

The supply company database 2810 may also store inventory management information 2830, such as quantity and the particulars of material inventory and material warranty information for such materials 2832. The warranty information for materials used in the project may be hashed 2834 and the resulting hash value may be stored in storage in the supply company database 2810. The hashed value 2834 may be passed to the management company database 2804 and then referenced on the persistent storage 2802. The supply company database 2810 may also store shipping management information 2836. This may include bill of lading histories 2838 and barcode, RFID values, UHF values and/or QR code scan histories 2840. The bills of lading (BOLs) for the project and the barcode/QR scan codes for delivered items for the projects may be hashed 2842 and the resulting hash value(s) passed to the management company database 2804 for reference on the persistent storage 2802. Further, confirmation of what was specified by designers was delivered to the construction site and installed according to the manufacturer's specifications so that a construction project can be placed under warranty.

A construction company database 2812 may store project information 2846, such as TMS #'s, GPS data and addresses for projects. The construction company database may also hold scheduling information 2848 for the project. This may include detail regarding workflow and timing. A hash value of the project schedule 2850 may be stored on the construction company database 2812, passed to the management company database 2804 and referenced on the persistent storage 2802. The construction company database 2812 may store worker information 2852. The worker information 2852 may include employee information 2854 for workers involved in projects. This employee information 2854 may include information regarding licenses for workers 2856, hire dates for workers 2858, employment end dates for workers 2860 and other information, such as names, photos, etc. The worker or labor information can include information that the worker or laborer is in compliance with applicable laws (including federal and state), in compliance with contractual obligations, properly licensed, of legal status, of sufficient experience, within application restrictions such as a limit on hours worked during a 24 hours period, authorized for the construction site or any combination. The worker or laborer information may be sortable by keys such as TMS # to identify workers for a project. The construction company database 2812 may also store scheduling information 2864 for workers. This information may be used to develop a worker/sequencing proposal that is hashed 2866 and the resulting hash value stored in the construction company database 2812. The hash value 2866 may be passed to the management company database 2804 and referenced on the persistent storage 2802. Worker sequencing data once the labor is completed 2868 may be hashed and the resulting hash value stored in the construction company database 2812 for a project. This hash value 2868 may be passed to the management company database 2804 and referenced on the persistent storage 2802.

Punch list management information 2870 may also be stored in the construction company database 2812. The punch list management information 2870 may include a hash of the punch list for a project 2871 and a hash of punch list releases for a project 2872. These hash values 2871 and 2872 may be passed to the management company database 2804 and referenced on the persistent storage 2802. The punch list information can be used for a determination of warranty requirement compliance.

Inspection management information 2874 may be stored in the construction company database 2812. Hashes of scheduled dates of inspections 2876, dates of actual inspections and results 2877 and failed inspection reports 2878 for a project may be stored in the construction company database. The hash values 2876, 2877 and 2878 may be passed to the management company database 2804 and referenced on the persistent storage 2802.

Hash values gathered and stored in the site supervisor database 2814 may be passed to the management company database 2804 and referenced on the persistent storage 2802. This may include hash values of information regarding dates and times of deliveries for a project 2880, delivery details for the project 2881 and delivery notes and delivery photos for the project 2882. The hash values may include hash values resulting from passing GPS information for wearables used in the project 2883, heart rate information gathered by wearables for the project 2884, failure reports from the wearables for the project 2885 through hash functions. Additionally hash values resulting from passing RFID tool usage information for the project 2886, security camera footage gathered by the site supervisor for the project 2887, weather data recorded by the site supervisor for the project 2888, hours information for when the site supervisor was active for the project through hash algorithms may be stored in the site supervisor database 2814, passed to the management company database 2804 and referenced on the persistent storage 2802. The values may also result from passing GPS location information for the system 2890, tracking information for delivery trucks 2892 and contractor power usage information 2894 through a hash function. Hash values 2890, 2892 and 2894 may be passed to the management company database 2804 and referenced on the persistent storage 2802.

Figure 29:
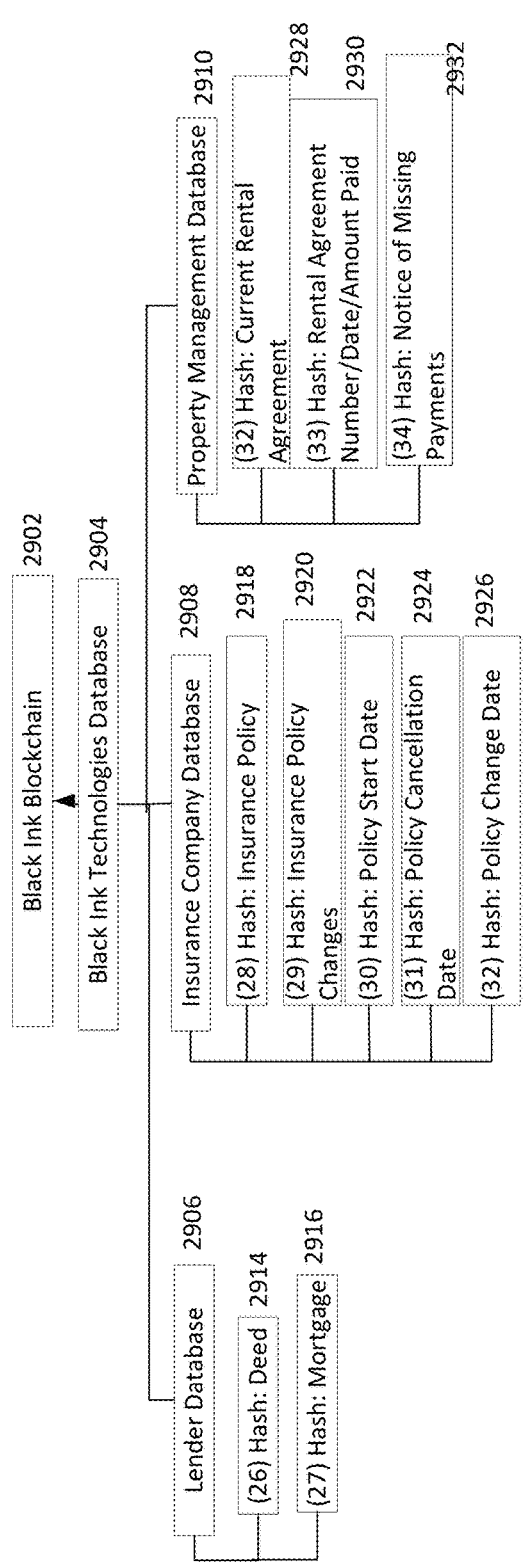

Information referenced on the distributed ledger may originate from third parties. FIG. 29 shows a diagram 2900 of additional sources of information from other stakeholders. For example, information may originate from a lender database 2906. For example, hashed versions of the deed for the construction site property 2914 and the mortgage 2916 on the construction site property may be stored in the lender database 2906, transferred to the management company database 2904 and referenced on the persistent storage 2902.

Information may originate from an insurance company database 2908. A hash of an insurance policy for the project 2918, a hash of any insurance policy changes for the project 2920, a hash of policy start date 2922, a hash of policy cancellation date 2924 and a hash of policy change dates 2926 may be stored in the insurance company database 2908. The resulting hash values 2918, 2920, 2922, 2924 and 2926 may be transferred to the management company database 2904 and referenced on the persistent storage 2902.

Information may also originate from a property management database 2910. Hashes of a current rental agreement 2928, rental agreement particulars 2930 (such as agreement number, dates and amount paid) and notice(s) of missed payments 2932 may be stored therein. Information can include utility consumption and expenses such as insurance, taxes, maintenance, and the like.

This hash values 2928, 2930 and 2932 may be added to the management company database 2904 and ultimately referenced on the persistent storage 2902.

Figure 30:
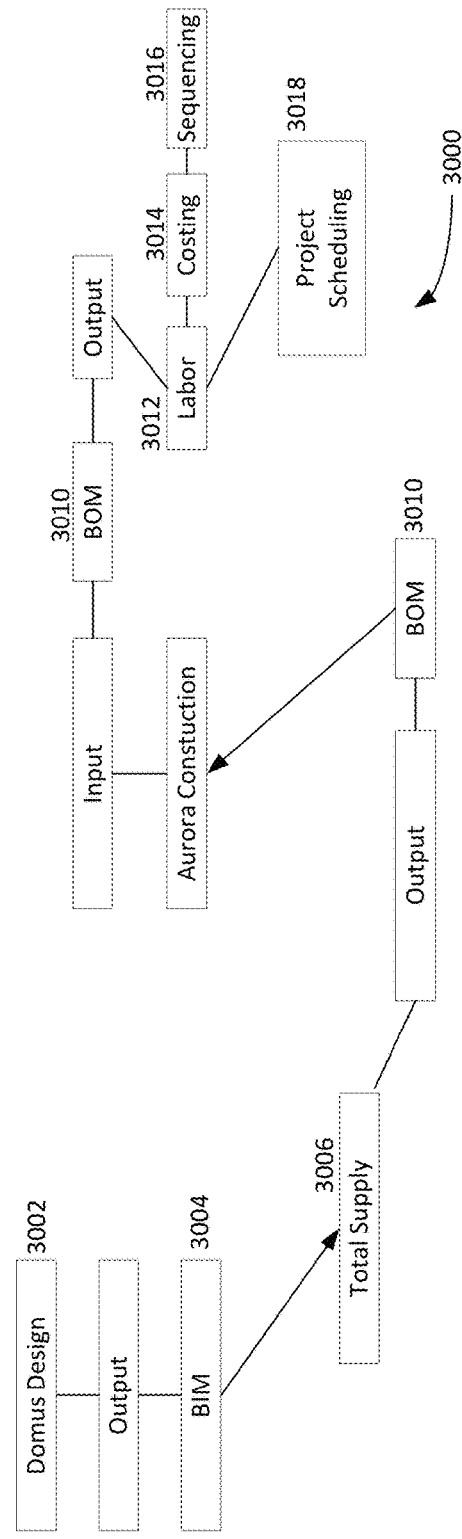
FIG. 30 shows an information flow from of the system.

FIG. 30 shows a diagram 3000 that captures information flow among the design company 3002, the supply company 3006 and the construction company 3012. As was mentioned above the design company 3002 generates a BIM 3004 for the construction project that is passed to the supply company 3006. The supply company 3006 uses information in the BIM 3004 to generate the BOM 3010. The BOM 3010 is then shared with the construction company 3012. The construction company 3012 develops a project schedule 3018. The project schedule 3018 specifies labor needs 3012 for the project, the costs for the labor 3014 and the sequencing of labor 3018 over the project.

Figures 31, 32:
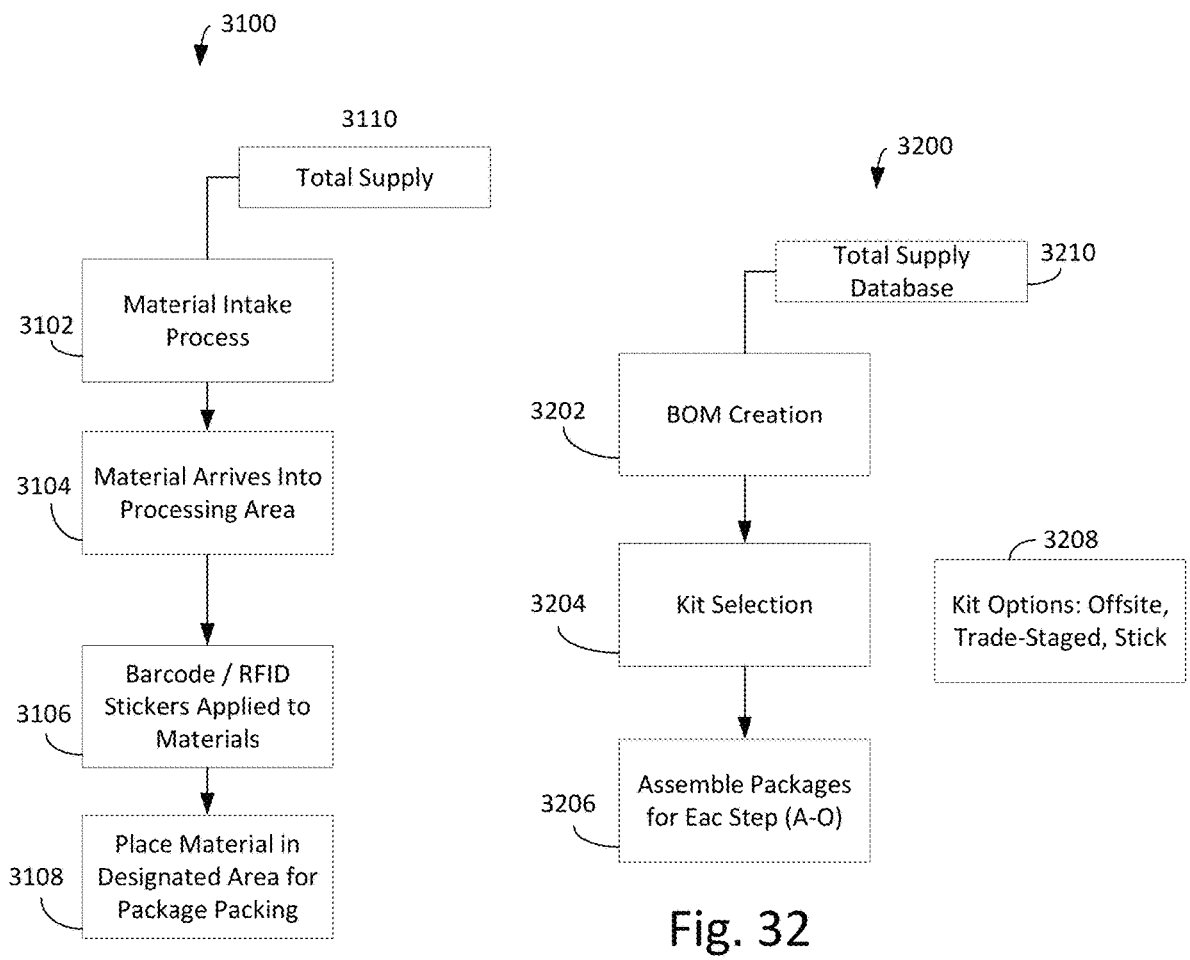
FIGS. 31-33 shows operations performed by system.

The supply company 3110 is responsible for the intake of materials specified in the BOM that are needed for the construction project. FIG. 31 shows a diagram 3100 of steps taken in the material intake process 3102. Materials arrive 3014 at a processing area of the supply company 3110 from the manufacturers and/or distributors. Items such as barcode stickers, QR code stickers, Bluetooth beacons, UHF stickers and/or RFID stickers are applied to the materials 3106 so that the materials may be identified and tracked. The materials with the stickers applied are placed in a designated area for packing 3108. The materials may then be packaged for shipment to the construction site.

As shown in the diagram of FIG. 32, the materials may be organized into kits for activities at the construction site. The BOM 3204 is created 3202 and processed to develop the set or group of materials that will be sent to the construction site. Different strategies 3208 may deployed to develop the set of materials. For example, the materials in the set may be staged based on the trade involved (e.g., electrical, plumbing, carpentry) so that each trade has its own set for the stage of construction. Thus, sets are selected 3204, and packages are developed for each step or stage of the construction project 3206.

Figure 33:
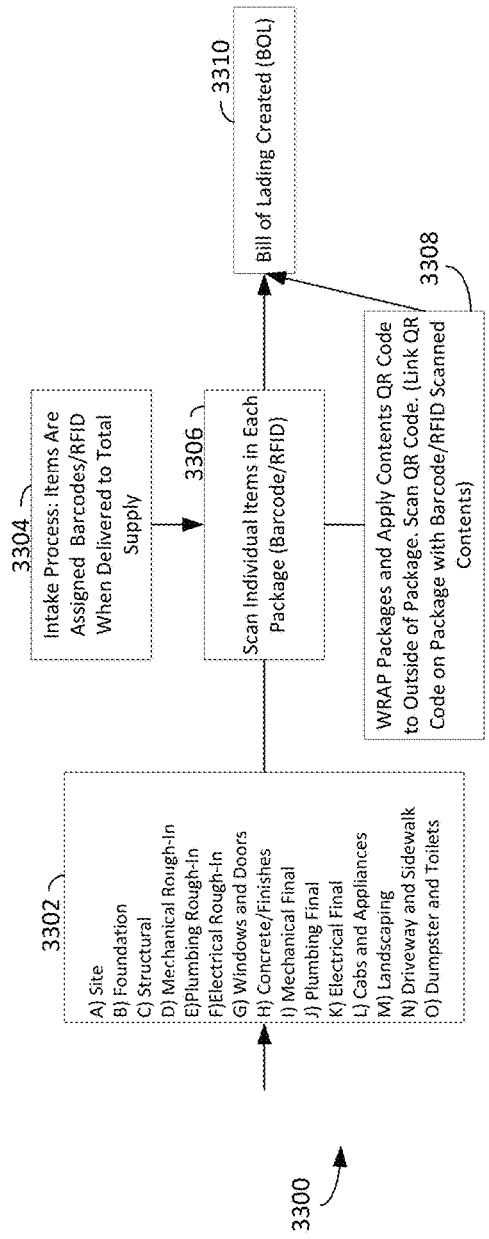

FIG. 33 shows a diagram 3300 depicting additional detail of activity performed by the supply company. The construction project schedule 3302 is organized into stages, such as site preparation, foundation, etc. as shown in FIG. 33. Items may be affixed, such as barcodes, QR codes, RFID identification, Bluetooth beacons and/or UHF identification when the items arrive at the supply company 3304. As was mentioned above, stickers may be affixed to the items to associate the codes with the items. The items in each package may be scanned to record what items are included in the packages 3306. The packages may be wrapped as needed and a QR code sticker may be affixed to the outside of each package 3308. The QR code for each package is scanned 3312. The process may then generate a BOL for each delivery 3310.

Figure 27:
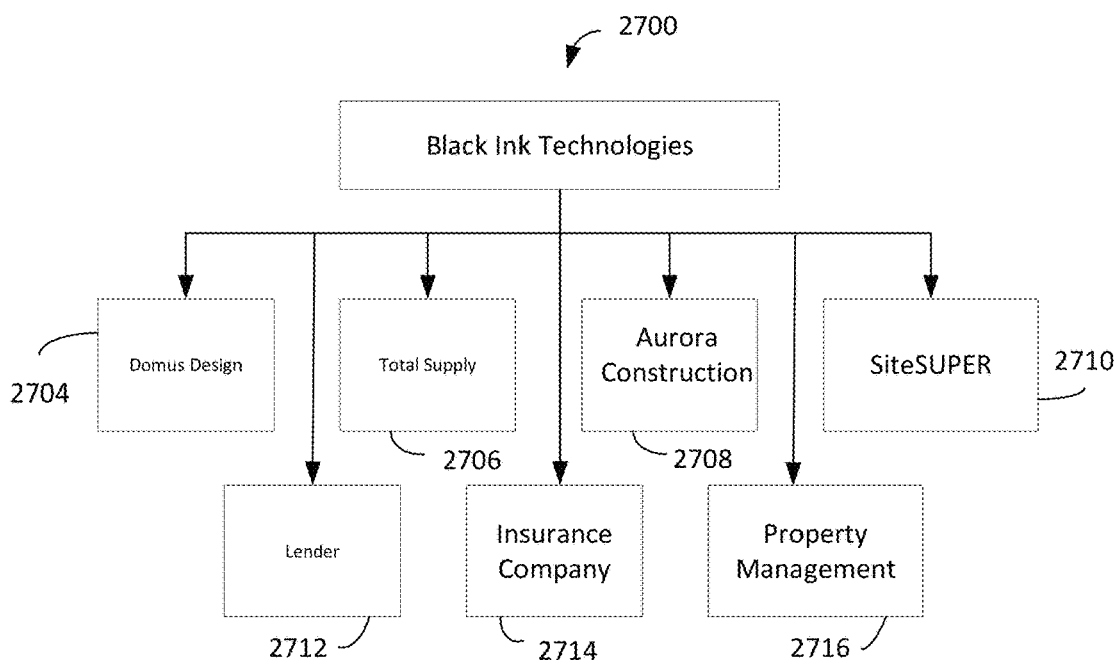
Figure 34:
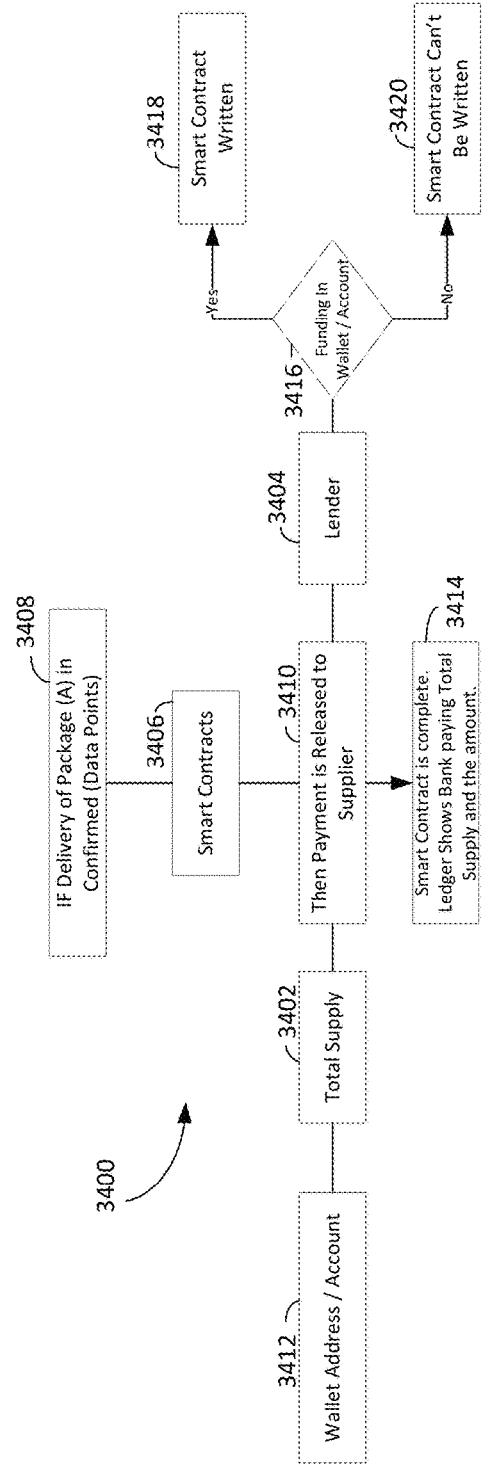
FIGS. 34-35 shows examples smart contracts.

Much of the interactions among the parties shown in FIG. 27 rely upon smart contracts that utilize persistent storage. FIG. 34 shows a diagram 3400 of a first example of interactions relating to a smart contract for the construction project. Suppose that the supply company 3402 makes a delivery to the construction site. Further suppose that the delivery is confirmed 3408 by information such as that gathered by the system as discussed above. The lender 3404 then releases payment 3410 to the supply company 3402. Payments can be made through third party funding, factoring, credit lines, loans or other financial option to assist with financing and cash flow management.

The payment may be made electronically, such as through crypto currencies, like Bitcoin or Ether, or via a stable coin whose value is pinned to an item like a paper currency or the like. A cryptocurrency is a digital currency built with cryptographic protocols that make transactions secure and difficult to forge. Other Suitable forms of electronic payment includes Automated Clearing House (ACH) payment, Electronic Funds Transfer (EFT), card payments, other types of bank transfers or other types of electronic wallet transfer. In the case where crypto-currency is used, the crypto-currency may be delivered to the digital wallet of the supply company at a specified wallet address or account 3412. The ledger may be updated to show that the contract is complete 3414. Payment requires that the lender has sufficient funding in their digital wallet 3416. If not, the smart contract will not be written on the persistent storage 3418. If there is sufficient funding, payment is made, and the contract is written onto the persistence storage as complete at 3420.

Figure 35:
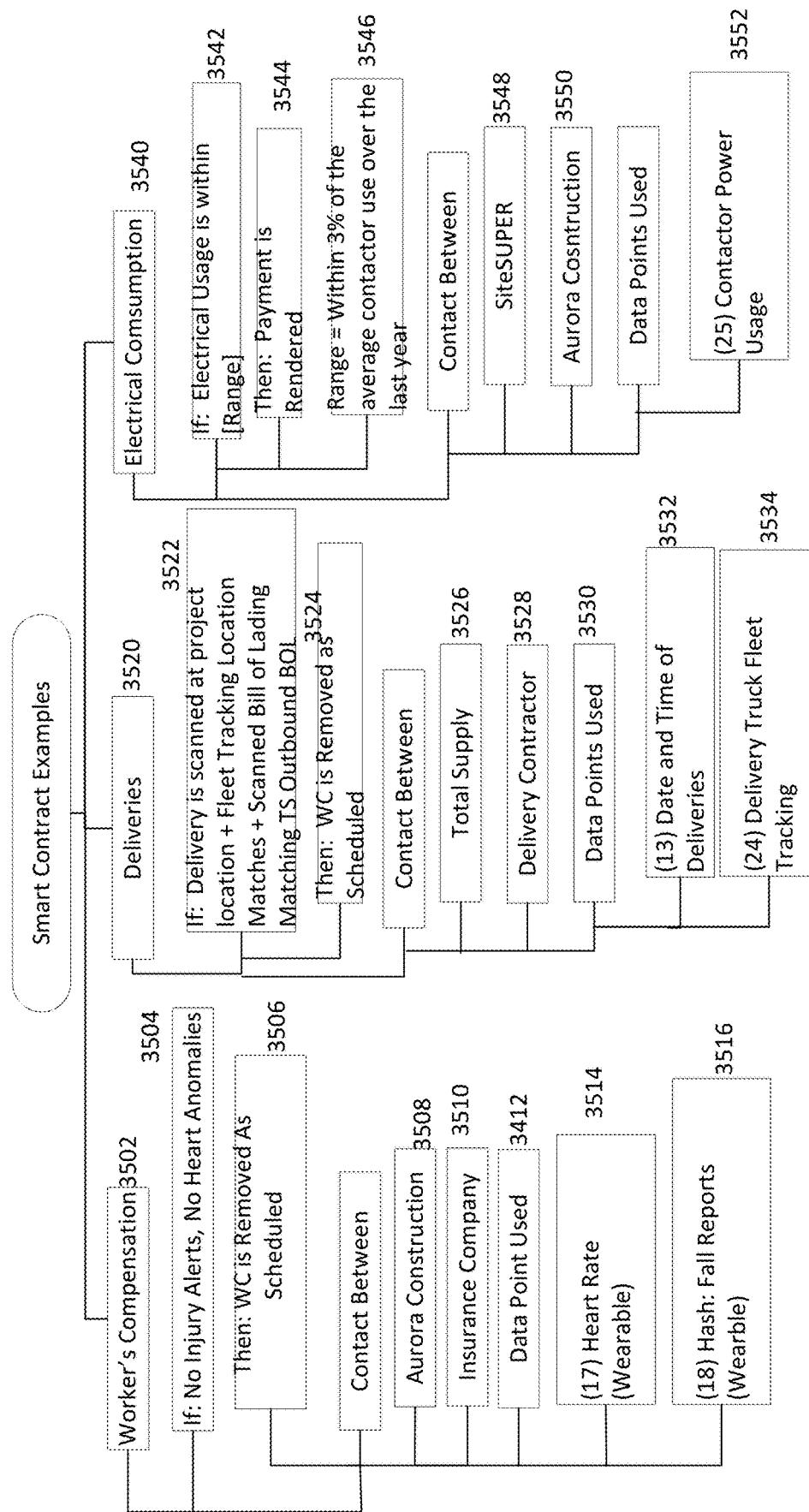

FIG. 35 depicts a diagram 3500 for multiple illustrative smart contracts. In a first illustrative smart contract, the smart contract concerns worker's compensation insurance 3502. The contract removes the insurance for a worker 3506 if there are no injury alerts and no heart rate abnormalities for a given worker 3504. The smart contract can be between entities such as employers (e.g. a construction company) 3508 and an insurance company 3510. The contract looks at the data points 3512 of the heart rate history 3514 gathered by a wearable for the worker and any fall reports 3516 from a wearable for the worker. As mentioned above, the wearables may include a gyroscope or other mechanism that provides data indicative of a fall. This data may be processed to identify data indicative or a fall or other incident where an injury may have occurred.

A second illustrative smart contract shown in FIG. 35 relates to payment for a delivery 3520. If a scan is made at the delivery site, if the fleet location tracking information matches the desired delivery site location and if the scanned BOL at the delivery site matches the outbound BOL from the supply company 3522, then payment from the supply company 3526 to the delivery contractor 3528 is made. Data 3530 used by this illustrative smart contract 3530 includes date and time of deliveries 3532 and delivery truck fleet tracking information 3534.

A third illustrative smart contract shown in FIG. 35 relates to electrical consumption 3540. If the electrical usage by a contractor of the construction company is within a range of 3% of the average contractor use over the past year 3542 and 3546, then payment is provided 3544 by the construction company 3550 to the system 3548. Power usage data 3552 can be reviewed.

There can be a relationship between the smart contracts and the project schedule. FIG. 36 depicts a flowchart 3600 illustrating steps performed relating to the project schedule and smart contracts. Initially, the project schedule is received 3602. As was discussed above, the construction company forms the project schedule based in part on the BIM and BOM. Based on the project schedule, smart contracts may be constructed that use the persistent storage for contractual arrangements associated with the construction project 3604. The smart contracts are implemented in software and in this case are used to provide electronic payments to parties 3606 for activities relating to the construction project using, for example, electronic payments, crypto currencies, fiat currencies and other forms of payments. The smart contracts may specify the conditions required for payment and may specify the amounts of payment.

FIG. 37 shows a flowchart 3700 depicting steps performed for construction work in the construction project. Initially a smart contract may be initiated that uses the blockchain-based distributed ledger, where the smart contract is for at least a portion of the construction work for the construction project 3702. An inspection of work performed under the contract takes place and information regarding the inspection is passed through a hash function resulting in a hash value. The hash value may be referenced on the blockchain-based persistent storage 3704. The information may include, for example, the name of the inspector, the date of the inspection, an identification of what was inspected, an indication of whether the inspection was passed, any inspection notes from the inspector and an identification of any defects that cause a fail inspection and how to remedy. A notice is received at the system that a portion of the project is complete 3706. The inspection information is assessed 3708. If the inspection information indicates that the inspection was passed 3710, then payment may be provided 3712 to the construction company via smart contract for the portion of the construction project. In contrast, if the inspection was unsuccessful, a notice of the failure and a notice of issues that need to be addressed may be sent, hashed and resulting hash value may be referenced on the blockchain-based persistent storage 3714 for review by the construction company. The construction company may then attempt to remediate the problems 3716 and repeat the above described steps beginning with a new inspection and reference to a hash value for information regarding the new inspection on the distributed ledger 3704.

Figures 38, 39:
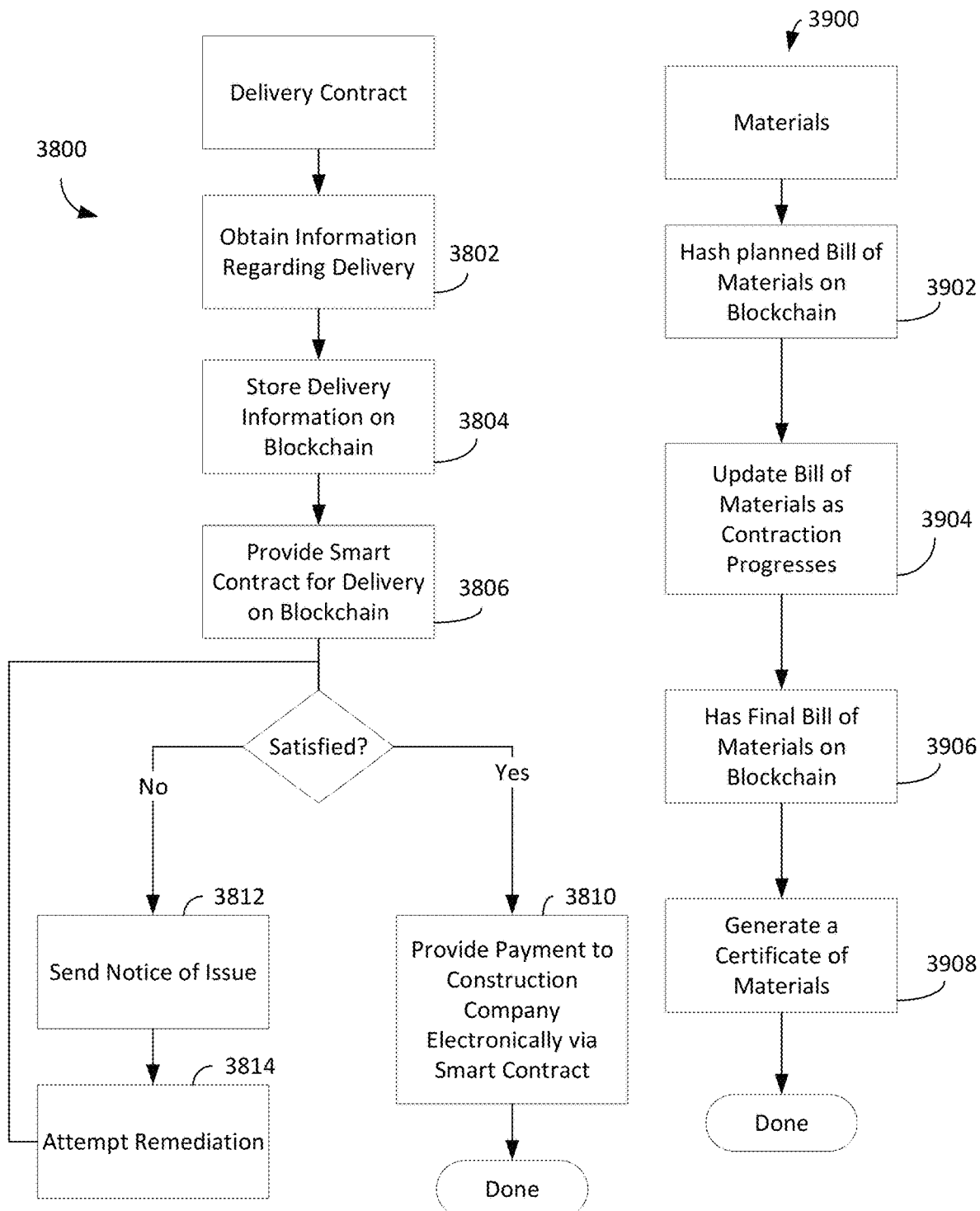

Smart contracts may also play a role with deliveries. FIG. 38 provides a flowchart 3800 concerning steps performed in relation to deliveries relating to such smart contracts. First, delivery and/or materials information is obtained regarding delivery to the construction site for the construction project 3802. The information obtained can include is the materials delivered match the BOM, manufacturer, supplier which can be confirmed by multiple parties.

The delivery information is hashed, and the resulting hash value is referenced on the blockchain-based persistent storage 3804. A smart contract is provided that uses the immutable distributed ledger 3806. A determination is made whether the conditions specified in the smart contract are satisfied 3808. If the conditions are satisfied, electronic payment for the delivery is realized 3810. If the conditions are not satisfied, notice of outstanding issues are sent and the delivery contractor may attempt to remedy the issues 3814. The process may then repeat beginning with step 3808 until the conditions are satisfied.

One of the benefits of the approach adopted by the exemplary embodiments described herein is that a complete record of materials used in the home of the construction project is maintained. FIG. 39 shows a flowchart of steps that are performed regarding such materials. Initially, the planned BOM generated by the supply company is hashed and the hash value is referenced on the blockchain-based persistent storage 3902 as described above. The BOM is updated as the construction progresses until the construction is complete 3904. When construction is complete, the final BOM is hashed and the hash value is referenced on the blockchain-based persistent storage 3906. The information in the final BOM is used to generate the certificate of materials provided to the owner of the home resulting from the construction project 3908.

As has been discussed above, worker's compensation insurance may be adjusted as workers are added and removed from the workforce for the construction project with the assistance of smart contracts. FIG. 40 provides a flowchart 4000 of steps performed relative to worker's compensation insurance. A smart contract is provided for worker's compensation insurance 4002 between the insurance provider and the construction company. Payment for the insurance may be held in escrow 4004 and funds may be added/deleted as warranted. When confirmation is received that workers are at the site to work 4006, the insurance is put in place and payment is received 4008 by the insurance provider for the insurance from escrow on behalf of the construction company. When notice is received that a worker or workers is/are no longer to be covered by the insurance 4010, a communication is generated to the insurance provider that no longer need coverage for the worker(s) 4012. An indication is received and hashed to produce a hash value that may be referenced on the blockchain-based persistent storage that the worker is no longer covered by the insurance 4014 and any adjustments in the insurance premiums may be made to the escrow account 4016.

Liens are often used in construction. The exemplary embodiments enable the triggering and releasing of such liens to be automated. FIG. 41 shows a flowchart 4100 of steps that may performed regarding liens. Initially, notice of a first event is received 4102 at the systems or at a server in a cloud environment. A programmatic determination is made that the event is a lien triggering event 4104. For example, suppose a supply company delivers items to a construction site. The supply company may have a lien on the items until payment is received. A communication is generated and sent that a lien is needed 4106. This communication may be sent to the involved parties. In some instances, where the lien is not in place, the communication may be sent to legal counsel or the like to perfect the lien. Notice of a second event may be received 4108. The second event may programmatically be determined to be a lien releasing event 4110. A release can be generated and sent to the proper parties at 4112.

Because of the tracking of construction progress and the automated scheduling, exemplary embodiments may provide for just in time (JIT) delivery. JIT delivery ensures that items are delivered when needed and are not delivered late causing delays. Moreover, JIT delivery ensures that items are not delivered too early and thus unnecessarily exposed to the elements, be susceptible to theft or occupy needed storage space. FIG. 42 shows a flowchart 4200 of steps performed to realize such JIT delivery scheduling. As has been discussed above, information regarding workflow is stored in storage 4202. The workflow specifies what items are needed and when the items are needed. The exemplary embodiments keep track of how a project is progressing and stores information in storage regarding the progress 4204. Based on this information delivery of items can be scheduled just in time 4206. A communication is generated and sent to prompt the delivery to occur when scheduled 4208.

The exemplary embodiments also support JIT labor where the labor arrives on site when they are needed. FIG. 43 shows a flowchart of steps that may be performed to realize JIT labor. The workflow for the project specifies what quantity of labor is needed and when the labor is needed. The workflow information is stored in storage 4302, as is information regarding the progress of the project 4304. Based on the stored workflow and progress information, labor needs are determined 4306. A communication is generated and sent to prompt the laborers to be scheduled for work on specified dates/times when they are needed 4308.

What is claimed is:

1. A computerized system for management of insurance risk and insurance events comprising:
    a kiosk having a kiosk computer readable medium uniquely associated with a construction site and in communication with a distributed ledger;
    a sensor in communications with the kiosk for detecting a presence of workers at a construction site, materials at the construction site, events and conditions occurring at the construction site;
    a set of non-transitory computer readable instructions included in the kiosk computer readable medium for:
        for each worker present at the construction site, determining an arrival time, a departure time, an amount of time worked and worker class,
        identifying a set of construction materials delivered to the construction site,
        detecting an installation action performed by a worker when installing the set of construction materials,
        detecting an insurance event,
        identifying a set of environmental conditions associated with the insurance event,
        associating the insurance event with the set of environmental conditions,
        creating an insurance record according to the insurance event, and transmitting the insurance record to a third party computer device.
2. The computerized system of claim 1 including a unique identifier taken from a group of a RFID, wireless signal, a digital identifier, an alphanumeric character, a graphic or any combination thereof.
3. The computerized system of claim 1 wherein the insurance event is a material loss according to a material identifier associated with a construction material.
4. The computerized system of claim 3 wherein the set of non-transitory computer readable instructions include instructions for detecting a set of material loss circumstances and appending the insurance record with the set of material loss circumstances.
5. The computerized system of claim 1 wherein the set of non-transitory computer readable instructions include instructions for detecting an installation deviation representing a deviation to an installation instruction included in a building information model stored on the kiosk, detecting a set of installation deviation circumstances, appending the insurance record with the set of installation deviation circumstances.
6. The computerized system of claim 5 including a drone having drone sensors and the set of non-transitory computer readable instructions include instructions for detecting the set of installation deviation circumstances using the drone.
7. The computerized system of claim 1 wherein the set of non-transitory computer readable instructions include instructions for assigning an equipment to at least one worker, determining if the equipment is removed from the construction site and appending the insurance record if the equipment is removed from the construction site.
8. The computerized system of claim 1 wherein computerized system of claim 1 wherein the insurance event is a worker related event.
9. The computerized system of claim 8 wherein the set of non-transitory computer readable instructions include instructions for detecting a set of worker injury circumstances associated with the worker related event and appending the insurance record with the set of worker injury circumstances.
10. The computerized system of claim 9 wherein the set of non-transitory computer readable instructions include instructions for receiving an insurance claim associated with the worker related event and determining if the insurance claims is consistent with the set of worker injury circumstances.
11. The computerized system of claim 1 wherein the set of non-transitory computer readable instructions include instructions for receiving a set of worker coverage information from an insurance computer system and determining if the set of worker coverage information is consistent with the set of workers located at the construction site.
12. The computerized system of claim 11 wherein the set of non-transitory computer readable instructions include instructions for determining is insurance coverage is inconsistent with the insurance claim made in response to an insurance event.
13. The computerized system of claim 1 wherein the set of non-transitory computer readable instructions include instructions for determining if the insurance event occurred within a construction site boundary associated with the construction site.
14. The computerized system of claim 1 wherein the set of non-transitory computer readable instructions include instructions for establishing a communications session with an insurance representative when an insurance event is detected.
15. The computerized system of claim 1 wherein the set of non-transitory computer readable instructions include instructions for transmitting a notification of the insurance event to a third-party computer device.

16. The computerized system of claim 1 wherein the set of non-transitory computer readable instructions include instructions for establishing a communications session with an event responder.

17. The computerized system of claim 16 wherein the event responder is associated with a communications system taken from the group consisting of a medical provider, first responder, Insurance representative, on-site manager or supervisor, off-site manager or supervisor, insurance entity, financial entity, owner, or any combination thereof.

18. The computerized system of claim 1 wherein the insurance event represents a construction material being removed from the construction site and the set of non-transitory computer readable instructions include instructions for detecting when the construction material is removed from the construction site.

19. The computerized system of claim 1 wherein the set of non-transitory computer readable instructions include instructions detecting an installation action performed by a worker when installing the set of construction materials.

20. The computerized system of claim 1 wherein the sensor is a video capture device and the set of non-transitory computer readable instructions include instructions recording video information upon the occurrence of an insurance event.

21. The computerized system of claim 1 including a weather station in communications with the kiosk configured to detect an actual installation condition and the set of non-transitory computer readable instructions include instructions for determining if the actual installation condition is outside a recommended installation condition included in a set of installation instructions.

22. The computerized system of claim 1 including:
a biometric sensor associated with a worker;
wherein the insurance event is an injury to a worker; and,
the set of non-transitory computer readable instructions include instructions for detecting a biometric value outside an acceptable biometric value range associated with the worker.

23. The computerized system of claim 1 including:
a video capture device; and;
the set of non-transitory computer readable instructions include instructions for confirming a worker has safety equipment properly installed according to video verification from the video capture device.

24. The computerized system of claim 23 including a biometric signature associated with a worker and the set of non-transitory computer readable instructions include instructions for confirming a worker has safety equipment properly installed according to the biometric signature and video capture device.

25. A computerized system for on-site management of accountability insurance risk and insurance events comprising:
a kiosk having a kiosk computer readable medium uniquely associated with a construction site;
a biometric sensor associated with a worker and in communications with the kiosk;
a set of non-transitory computer readable instructions included in the kiosk computer readable medium for:
detecting an insurance event according to the biometric sensor, and,
creating an insurance record according to the insurance event and transmitting the insurance record to an insurance computer system.

26. The computerized system of claim 25 wherein the set of non-transitory computer readable instructions include instructions for detecting a biometric value outside an acceptable biometric value range associated with the worker.

27. The computerized system of claim 26 wherein the set of non-transitory computer readable instructions include instructions for storing the material arrival record on a distributed ledger.

28. The computerized system of claim 26 wherein the set of non-transitory computer readable instructions include instructions for transmitting the material arrival record to an insurance computer system.

29. The computerized system of claim 26 wherein the set of non-transitory computer readable instructions include instructions for detecting an installation action performed by a worker when installing a set of construction materials, determining a labor cost associated with the installation action and increasing the coverage value according to the labor cost.

30. The computerized system of claim 29 wherein the set of non-transitory computer readable instructions include instructions for storing an increased replacement costs according to the coverage value on a distributed ledger.

31. The computerized system of claim 30 wherein the set of non-transitory computer readable instructions include instructions for transmitting the increased replacement costs to an insurance computer system.

* * * * *